(12) United States Patent
Muller

(10) Patent No.: US 10,583,232 B2
(45) Date of Patent: Mar. 10, 2020

(54) CATHETER PUMP WITH OFF-SET MOTOR POSITION

(71) Applicant: TC1 LLC, St. Paul, MN (US)

(72) Inventor: Paul F. Muller, San Carlos, CA (US)

(73) Assignee: TC1 LLC, St. Paul, MN (US)

( * ) Notice: Subject to any disclaimer, the term of this patent is extended or adjusted under 35 U.S.C. 154(b) by 487 days.

(21) Appl. No.: 15/303,711

(22) PCT Filed: Apr. 15, 2015

(86) PCT No.: PCT/US2015/025959
§ 371 (c)(1),
(2) Date: Oct. 12, 2016

(87) PCT Pub. No.: WO2015/160942
PCT Pub. Date: Oct. 22, 2015

(65) Prior Publication Data
US 2017/0028115 A1 Feb. 2, 2017

Related U.S. Application Data

(60) Provisional application No. 61/979,876, filed on Apr. 15, 2014.

(51) Int. Cl.
*A61M 1/12* (2006.01)
*A61M 1/10* (2006.01)

(52) U.S. Cl.
CPC ........ *A61M 1/1034* (2014.02); *A61M 1/1029* (2014.02); *A61M 1/101* (2013.01); *A61M 1/102* (2014.02); *A61M 1/1024* (2014.02); *A61M 1/1031* (2014.02); *A61M 1/1082* (2014.02); *A61M 1/1084* (2014.02); *A61M 1/122* (2014.02); *A61M 1/125* (2014.02)

(58) Field of Classification Search
USPC .......................................... 600/16
See application file for complete search history.

(56) References Cited

U.S. PATENT DOCUMENTS 1,902,418 A   3/1933  Pilgrim
2,356,659 A  10/1942  Aguiar
(Continued)

FOREIGN PATENT DOCUMENTS

CA    2701810    4/2009
EP    0 533 432  9/1992
(Continued)

OTHER PUBLICATIONS

Abiomed, "Impella 5.0 with the Impella Console, Circulatory Support System, Instructions for Use & Clinical Reference Manual," Jun. 2010, in 122 pages.
(Continued)

*Primary Examiner* — Nicole F Lavert
(74) *Attorney, Agent, or Firm* — Armstrong Teasdale LLP

(57) ABSTRACT

A catheter pump assembly is provided that includes an elongate body, an elongate flexible shaft disposed in the elongate body, and an impeller coupled with the distal end of the elongate flexible shaft. The drive system includes a drive component, a motor and a tension member. The tension member is coupled with the motor and the drive component and to cause the drive component to rotate, and thereby to cause the impeller to rotate.

10 Claims, 22 Drawing Sheets

(56) References Cited

U.S. PATENT DOCUMENTS

| | | |
|---|---|---|
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,896,926 A | 7/1959 | Chapman |
| 2,935,068 A | 5/1960 | Donaldson |
| 3,080,824 A | 3/1963 | Boyd et al. |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,115,040 A | 9/1978 | Knorr |
| 4,129,129 A | 12/1978 | Amrine |
| 4,135,253 A | 1/1979 | Reich et al. |
| 4,143,425 A | 3/1979 | Runge |
| 4,149,535 A | 4/1979 | Volder |
| 4,304,524 A | 12/1981 | Coxon et al. |
| 4,382,199 A | 5/1983 | Isaacson |
| 4,392,836 A | 7/1983 | Sugawara |
| 4,458,366 A | 7/1984 | MacGregor |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett |
| 4,686,982 A | 8/1987 | Nash |
| 4,696,667 A | 9/1987 | Masch |
| 4,704,121 A | 11/1987 | Moise |
| 4,728,319 A | 3/1988 | Masch |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffman et al. |
| 5,021,048 A | 6/1991 | Buckholtz |
| 5,045,072 A | 9/1991 | Castillo et al. |
| 5,049,134 A | 9/1991 | Golding et al. |
| 5,061,256 A | 10/1991 | Wampler |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,292 A | 5/1992 | Hwang et al. |
| 5,112,349 A | 5/1992 | Summers et al. |
| 5,129,883 A | 7/1992 | Black |
| 5,142,155 A | 8/1992 | Mauze et al. |
| 5,147,186 A | 9/1992 | Buckholtz |
| 5,163,910 A | 11/1992 | Schwartz et al. |
| 5,169,378 A | 12/1992 | Figuera |
| 5,171,212 A | 12/1992 | Buck et al. |
| 5,190,528 A | 3/1993 | Fonger et al. |
| 5,195,960 A | 3/1993 | Hossain et al. |
| 5,201,679 A | 4/1993 | Velte et al. |
| 5,211,546 A | 5/1993 | Isaacson et al. |
| 5,221,270 A | 6/1993 | Parker |
| 5,234,407 A | 8/1993 | Teirstein et al. |
| 5,234,416 A | 8/1993 | Macaulay et al. |
| 5,290,227 A | 3/1994 | Pasque |
| 5,300,112 A | 4/1994 | Barr |
| 5,312,341 A | 5/1994 | Turi |
| 5,344,443 A | 9/1994 | Palma et al. |
| 5,346,458 A | 9/1994 | Affeld |
| 5,360,317 A | 11/1994 | Clausen et al. |
| 5,376,114 A | 12/1994 | Jarvik |
| 5,393,197 A | 2/1995 | Lemont et al. |
| 5,393,207 A | 2/1995 | Maher et al. |
| 5,405,341 A | 4/1995 | Martin |
| 5,405,383 A | 4/1995 | Barr |
| 5,415,637 A | 5/1995 | Khosravi |
| 5,437,541 A | 8/1995 | Vainrub et al. |
| 5,449,342 A | 9/1995 | Hirose et al. |
| 5,458,459 A | 10/1995 | Hubbard et al. |
| 5,490,763 A | 2/1996 | Abrams et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,534,287 A | 7/1996 | Lukic |
| 5,554,114 A | 9/1996 | Wallace et al. |
| 5,588,812 A | 12/1996 | Taylor et al. |
| 5,609,574 A | 3/1997 | Kaplan et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman et al. |
| 5,702,418 A | 12/1997 | Ravenscroft |
| 5,704,926 A | 1/1998 | Sutton |
| 5,707,218 A | 1/1998 | Maher et al. |
| 5,722,930 A | 3/1998 | Larson et al. |
| 5,725,513 A | 3/1998 | Ju et al. |
| 5,725,570 A | 3/1998 | Heath |
| 5,730,628 A | 3/1998 | Hawkins |
| 5,735,897 A | 4/1998 | Buirge |
| 5,738,649 A | 4/1998 | Macoviak |
| 5,741,234 A | 4/1998 | Aboul-Hosn |
| 5,741,429 A | 4/1998 | Donadio, III et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,776,161 A | 7/1998 | Globerman |
| 5,776,190 A | 7/1998 | Jarvik |
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,859,482 A | 1/1999 | Crowell et al. |
| 5,868,702 A | 2/1999 | Stevens |
| 5,868,703 A | 2/1999 | Bertolero |
| 5,888,241 A | 3/1999 | Jarvik |
| 5,888,242 A | 3/1999 | Antaki et al. |
| 5,911,685 A | 6/1999 | Siess et al. |
| 5,921,913 A | 7/1999 | Siess |
| 5,941,813 A | 8/1999 | Sievers et al. |
| 5,951,263 A | 9/1999 | Taylor et al. |
| 5,957,941 A | 9/1999 | Ream |
| 5,964,694 A | 10/1999 | Siess et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,027,863 A | 2/2000 | Donadio, III et al. |
| 6,053,705 A | 4/2000 | Schob et al. |
| 6,056,719 A | 5/2000 | Mickley |
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,106,494 A | 8/2000 | Saravia et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |

(56) References Cited

U.S. PATENT DOCUMENTS

| | | |
|---|---|---|
| 6,132,363 A | 10/2000 | Freed et al. |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,190,357 B1 | 2/2001 | Ferrari et al. |
| 6,200,260 B1 | 3/2001 | Bolling |
| 6,210,133 B1 | 4/2001 | Aboul-Hosn et al. |
| 6,210,318 B1 | 4/2001 | Lederman |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,228,063 B1 | 5/2001 | Aboul-Hosn |
| 6,234,960 B1 | 5/2001 | Aboul-Hosn et al. |
| 6,234,995 B1 | 5/2001 | Peacock, III |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,454,775 B1 | 9/2002 | Demarais et al. |
| 6,468,298 B1 | 10/2002 | Pelton |
| 6,503,224 B1 | 1/2003 | Forman et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | de Blanc et al. |
| 6,565,598 B1 | 5/2003 | Lootz |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,652,548 B2 | 11/2003 | Evans et al. |
| 6,660,014 B2 | 12/2003 | Demarais et al. |
| 6,673,105 B1 | 1/2004 | Chen |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Grundeman et al. |
| 6,794,784 B2 | 9/2004 | Takahashi et al. |
| 6,794,789 B2 | 9/2004 | Siess et al. |
| 6,814,713 B2 | 11/2004 | Aboul-Hosn et al. |
| 6,817,836 B2 | 11/2004 | Nose et al. |
| 6,818,001 B2 | 11/2004 | Wulfman et al. |
| 6,860,713 B2 | 3/2005 | Hoover |
| 6,866,625 B1 | 3/2005 | Avre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,901,289 B2 | 5/2005 | Dahl et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,229,258 B2 | 6/2007 | Wood et al. |
| 7,241,257 B1 | 7/2007 | Ainsworth et al. |
| 7,262,531 B2 | 8/2007 | Li et al. |
| 7,264,606 B2 | 9/2007 | Jarvik et al. |
| 7,267,667 B2 | 9/2007 | Houde et al. |
| 7,284,956 B2 | 10/2007 | Nose et al. |
| 7,288,111 B1 | 10/2007 | Holloway et al. |
| 7,290,929 B2 | 11/2007 | Smith et al. |
| 7,329,236 B2 | 2/2008 | Keren et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride et al. |
| 7,469,716 B2 | 12/2008 | Parrino et al. |
| 7,491,163 B2 | 2/2009 | Viole et al. |
| 7,534,258 B2 | 5/2009 | Gomez |
| 7,605,298 B2 | 10/2009 | Bechert et al. |
| 7,619,560 B2 | 11/2009 | Penna |
| 7,633,193 B2 | 12/2009 | Masoudipour et al. |
| 7,645,225 B2 | 1/2010 | Medvedev et al. |
| 7,657,324 B2 | 2/2010 | Westlund et al. |
| 7,682,673 B2 | 3/2010 | Houston et al. |
| 7,722,568 B2 | 5/2010 | Lenker et al. |
| 7,731,675 B2 | 6/2010 | Aboul-Hosn et al. |
| 7,736,296 B2 | 6/2010 | Siess et al. |
| 7,758,521 B2 | 7/2010 | Morris et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,811,279 B2 | 10/2010 | John |
| 7,819,833 B2 | 10/2010 | Ainsworth et al. |
| 7,820,205 B2 | 10/2010 | Takakusagi et al. |
| 7,828,710 B2 | 11/2010 | Shifflette |
| 7,841,976 B2 | 11/2010 | McBride et al. |
| 7,878,967 B1 | 2/2011 | Khanal |
| 7,918,828 B2 | 4/2011 | Lundgaard et al. |
| 7,927,068 B2 | 4/2011 | McBride et al. |
| 7,935,102 B2 | 5/2011 | Breznock et al. |
| 7,942,804 B2 | 5/2011 | Khaw |
| 7,942,844 B2 | 5/2011 | Moberg et al. |
| 7,955,365 B2 | 6/2011 | Doty |
| 7,993,259 B2 | 8/2011 | Kang et al. |
| 7,998,054 B2 | 8/2011 | Bolling |
| 7,998,190 B2 | 8/2011 | Gharib et al. |
| 8,012,079 B2 | 9/2011 | Delgado |
| 8,025,647 B2 | 9/2011 | Siess et al. |
| 8,079,948 B2 | 12/2011 | Shifflette |

(56) References Cited

U.S. PATENT DOCUMENTS

| | | |
|---|---|---|
| 8,110,267 B2 | 2/2012 | Houston et al. |
| 8,114,008 B2 | 2/2012 | Hidaka et al. |
| 8,123,669 B2 | 2/2012 | Siess et al. |
| 8,177,703 B2 | 5/2012 | Smith et al. |
| 8,206,350 B2 | 6/2012 | Mann et al. |
| 8,209,015 B2 | 6/2012 | Glenn |
| 8,216,122 B2 | 7/2012 | Kung |
| 8,235,943 B2 | 8/2012 | Breznock et al. |
| 8,236,040 B2 | 8/2012 | Mayberry et al. |
| 8,236,044 B2 | 8/2012 | Robaina |
| 8,255,050 B2 | 8/2012 | Mohl |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,329,913 B2 | 12/2012 | Murata et al. |
| 8,333,687 B2 | 12/2012 | Farnan et al. |
| 8,348,991 B2 | 1/2013 | Weber et al. |
| 8,364,278 B2 | 1/2013 | Pianca et al. |
| 8,376,707 B2 | 2/2013 | McBride et al. |
| 8,382,818 B2 | 2/2013 | Davis et al. |
| 8,388,565 B2 | 3/2013 | Shifflette |
| 8,409,128 B2 | 4/2013 | Ferrari |
| 8,414,645 B2 | 4/2013 | Dwork et al. |
| 8,439,859 B2 | 5/2013 | Pfeffer et al. |
| 8,449,443 B2 | 5/2013 | Rodefeld |
| 8,485,961 B2 | 7/2013 | Campbell et al. |
| 8,489,190 B2 | 7/2013 | Pfeffer et al. |
| 8,535,211 B2 | 9/2013 | Campbell et al. |
| 8,540,615 B2 | 9/2013 | Aboul-Hosn et al. |
| 8,545,379 B2 | 10/2013 | Marseille et al. |
| 8,545,380 B2 | 10/2013 | Farnan et al. |
| 8,579,858 B2 | 11/2013 | Reitan |
| 8,585,572 B2 | 11/2013 | Mehmanesh |
| 8,591,393 B2 | 11/2013 | Walters et al. |
| 8,597,170 B2 | 12/2013 | Walters et al. |
| 8,617,239 B2 | 12/2013 | Reitan |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,784,441 B2 | 7/2014 | Rosenbluth et al. |
| 8,790,236 B2 | 7/2014 | LaRose et al. |
| 8,795,576 B2 | 8/2014 | Tao et al. |
| 8,801,590 B2 | 8/2014 | Mohl |
| 8,814,776 B2 | 8/2014 | Hastie et al. |
| 8,814,933 B2 | 8/2014 | Siess |
| 8,849,398 B2 | 9/2014 | Evans |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 9,089,634 B2 | 7/2015 | Schumacher et al. |
| 9,089,670 B2 | 7/2015 | Scheckel |
| 9,162,017 B2 | 10/2015 | Evans et al. |
| 9,217,442 B2 | 12/2015 | Wiessler et al. |
| 9,308,302 B2 | 4/2016 | Zeng |
| 9,314,558 B2 | 4/2016 | Er |
| 9,327,067 B2 | 5/2016 | Zeng et al. |
| 9,328,741 B2 | 5/2016 | Liebing |
| 9,358,330 B2 | 6/2016 | Schumacher |
| 2002/0107506 A1 | 8/2002 | McGuckin, Jr. et al. |
| 2003/0018380 A1 | 1/2003 | Craig et al. |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2005/0049696 A1 | 3/2005 | Siess et al. |
| 2005/0085683 A1 | 4/2005 | Bolling et al. |
| 2005/0113631 A1 | 5/2005 | Bolling et al. |
| 2005/0137680 A1 | 6/2005 | Ortiz et al. |
| 2005/0165269 A9 | 7/2005 | Aboul-Hosn et al. |
| 2005/0250975 A1 | 11/2005 | Carrier et al. |
| 2006/0018943 A1 | 1/2006 | Bechert et al. |
| 2006/0058869 A1 | 3/2006 | Olson et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0264695 A1 | 11/2006 | Viole et al. |
| 2006/0270894 A1 | 11/2006 | Viole et al. |
| 2007/0100314 A1 | 5/2007 | Keren et al. |
| 2008/0004645 A1 | 1/2008 | To et al. |
| 2008/0103442 A1 | 5/2008 | Kesten et al. |
| 2008/0103516 A1 | 5/2008 | Wulfman et al. |
| 2008/0119943 A1 | 5/2008 | Armstrong et al. |
| 2008/0132748 A1 | 6/2008 | Shifflete |
| 2008/0167679 A1 | 7/2008 | Papp |
| 2008/0275290 A1 | 11/2008 | Viole et al. |
| 2009/0018567 A1 | 1/2009 | Escudero et al. |
| 2009/0024085 A1 | 1/2009 | To et al. |
| 2009/0099638 A1 | 4/2009 | Grewe |
| 2009/0112312 A1 | 4/2009 | LaRose et al. |
| 2009/0118567 A1 | 5/2009 | Siess |
| 2009/0182188 A1 | 7/2009 | Marseille et al. |
| 2009/0234378 A1 | 9/2009 | Escudero et al. |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0127871 A1 | 5/2010 | Pontin |
| 2010/0210895 A1 | 8/2010 | Aboul-Hosn et al. |
| 2010/0268017 A1 | 10/2010 | Siess |
| 2010/0274330 A1 | 10/2010 | Burwell et al. |
| 2010/0286791 A1 | 11/2010 | Goldsmith |
| 2011/0071338 A1 | 3/2011 | McBride et al. |
| 2011/0076439 A1 | 3/2011 | Zeilon |
| 2011/0152906 A1 | 6/2011 | Escudero et al. |
| 2011/0152907 A1 | 6/2011 | Escudero et al. |
| 2011/0237863 A1 | 9/2011 | Ricci et al. |
| 2012/0004495 A1 | 1/2012 | Bolling |
| 2012/0029265 A1 | 2/2012 | LaRose et al. |
| 2012/0059213 A1 | 3/2012 | Spence |
| 2012/0109172 A1* | 5/2012 | Schmitz .............. A61B 17/16 606/170 |
| 2012/0142994 A1 | 6/2012 | Toellner |
| 2012/0172654 A1 | 7/2012 | Bates |
| 2012/0178986 A1* | 7/2012 | Campbell ............. A61M 1/101 600/16 |
| 2012/0184803 A1 | 7/2012 | Simon et al. |
| 2012/0224970 A1 | 9/2012 | Schumacher et al. |
| 2012/0226097 A1 | 9/2012 | Smith et al. |
| 2012/0234411 A1 | 9/2012 | Scheckel |
| 2012/0245404 A1 | 9/2012 | Smith et al. |
| 2012/0265002 A1 | 10/2012 | Roehn et al. |
| 2013/0041202 A1 | 2/2013 | Toellner |
| 2013/0053622 A1 | 2/2013 | Corbett |
| 2013/0053623 A1 | 2/2013 | Evans et al. |
| 2013/0066140 A1 | 3/2013 | McBride et al. |
| 2013/0085318 A1 | 4/2013 | Toellner |
| 2013/0096364 A1 | 4/2013 | Reichenbach et al. |
| 2013/0103063 A1 | 4/2013 | Escudero et al. |
| 2013/0106212 A1 | 5/2013 | Nakazumi et al. |
| 2013/0129503 A1 | 5/2013 | McBride et al. |
| 2013/0138205 A1 | 5/2013 | Kushwaha et al. |
| 2013/0204362 A1 | 8/2013 | Toellner et al. |
| 2013/0209292 A1 | 8/2013 | Baykut et al. |
| 2013/0237744 A1 | 9/2013 | Pfeffer et al. |
| 2013/0245360 A1 | 9/2013 | Schumacher |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2013/0345492 A1 | 12/2013 | Pfeffer et al. |
| 2014/0005467 A1 | 1/2014 | Farnan et al. |
| 2014/0010686 A1 | 1/2014 | Tanner et al. |
| 2014/0012065 A1 | 1/2014 | Fitzgerald et al. |
| 2014/0039465 A1 | 2/2014 | Schulz et al. |
| 2014/0067057 A1 | 3/2014 | Callaway et al. |
| 2014/0088455 A1 | 3/2014 | Christensen et al. |
| 2014/0148638 A1 | 5/2014 | LaRose et al. |
| 2014/0163664 A1 | 6/2014 | Goldsmith |
| 2014/0255176 A1 | 9/2014 | Bredenbreuker et al. |
| 2014/0275725 A1 | 9/2014 | Schenck et al. |
| 2014/0275726 A1 | 9/2014 | Zeng et al. |

(56) References Cited

U.S. PATENT DOCUMENTS

| | | | |
|---|---|---|---|
| 2014/0276948 A1* | 9/2014 | Zirps | A61B 34/73 606/130 |
| 2014/0301822 A1 | 10/2014 | Scheckel | |
| 2014/0303596 A1 | 10/2014 | Schumacher et al. | |
| 2015/0025558 A1 | 1/2015 | Wulfman et al. | |
| 2015/0031936 A1 | 1/2015 | LaRose et al. | |
| 2015/0051435 A1 | 2/2015 | Siess et al. | |
| 2015/0051436 A1 | 2/2015 | Spanier et al. | |
| 2015/0080743 A1 | 3/2015 | Siess | |
| 2015/0087890 A1 | 3/2015 | Spanier et al. | |
| 2015/0141738 A1 | 5/2015 | Toellner et al. | |
| 2015/0141739 A1 | 5/2015 | Hsu et al. | |
| 2015/0151032 A1 | 6/2015 | Voskoboynikov | |
| 2015/0209498 A1 | 7/2015 | Franono et al. | |
| 2015/0250935 A1 | 9/2015 | Anderson et al. | |
| 2015/0290372 A1 | 10/2015 | Muller et al. | |
| 2015/0343179 A1 | 12/2015 | Schumacher et al. | |
| 2016/0184500 A1 | 6/2016 | Zeng | |
| 2016/0250399 A1 | 9/2016 | Tiller et al. | |
| 2016/0250400 A1 | 9/2016 | Schumacher et al. | |
| 2016/0256620 A1 | 9/2016 | Scheckel et al. | |

FOREIGN PATENT DOCUMENTS

| | | |
|---|---|---|
| EP | 1 207 934 | 5/2002 |
| EP | 1 393 762 A1 | 3/2004 |
| EP | 1 591 079 A1 | 11/2005 |
| EP | 2 263 732 | 12/2010 |
| EP | 2 298 374 A1 | 3/2011 |
| FR | 2267800 | 4/1974 |
| GB | 2 239 675 A | 7/1991 |
| JP | S48-23295 | 3/1973 |
| JP | 06-114101 | 4/1994 |
| JP | 10-099447 | 4/1998 |
| TW | 500877 | 9/2002 |
| WO | WO 89/05164 | 6/1989 |
| WO | WO 95/26695 | 10/1995 |
| WO | WO 97/15228 | 5/1997 |
| WO | WO 97/37697 | 10/1997 |
| WO | WO 00/12148 | 3/2000 |
| WO | WO 00/19097 | 4/2000 |
| WO | WO 00/43062 | 7/2000 |
| WO | WO 00/61207 | 10/2000 |
| WO | WO 00/69489 | 11/2000 |
| WO | WO 01/17581 A2 | 3/2001 |
| WO | WO 01/24867 | 4/2001 |
| WO | WO 02/070039 | 9/2002 |
| WO | WO 03/103745 | 12/2003 |
| WO | WO 2005/089674 | 9/2005 |
| WO | WO 2005/123158 | 12/2005 |
| WO | WO 2009/073037 | 6/2009 |
| WO | WO 2009/076460 A2 | 6/2009 |
| WO | WO 2010/127871 | 11/2010 |
| WO | WO 2010/133567 | 11/2010 |
| WO | WO 2010/149393 | 12/2010 |
| WO | WO 2011/035926 | 3/2011 |
| WO | WO 2011/035929 | 3/2011 |
| WO | WO 2011/039091 A1 | 4/2011 |
| WO | WO 2011/076439 | 6/2011 |
| WO | WO 2011/089022 | 7/2011 |
| WO | WO 2012/007140 | 1/2012 |
| WO | WO 2012/007141 | 1/2012 |
| WO | WO 2013/148697 A1 | 10/2013 |
| WO | WO 2013/160407 A1 | 10/2013 |
| WO | WO 2014/019274 A1 | 2/2014 |
| WO | WO 2015/063277 | 5/2015 |

OTHER PUBLICATIONS

Abiomed—Recovering Hearts. Saving Lives., Impella 2.5 System, Instructions for Use, Jul. 2007, in 86 sheets.
Aboul-Hosn et al., "The Hemopump: Clinical Results and Future Applications", Assisted Circulation 4, 1995, in 14 pages.
Barras et al., "Nitinol-Its Use in Vascular Surgery and Other Applications," Eur. J. Vasc. Endovasc. Surg., 2000, pp. 564-569; vol. 19.
Biscarini et al., "Enhanced Nitinol Properties for Biomedical Applications," Recent Patents on Biomedical Engineering, 2008, pp. 180-196, vol. 1(3).
Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.
Compendium of Technical and Scientific Information for the Hemopump Temporary Cardiac Assist System, Johnson & Johnson Interventional Systems, 1988, in 15 pages.
Dekker et al., "Efficacy of a New Intraaortic Propeller Pump vs the Intraaortic Balloon Pump*, An Animal Study", Chest, Jun. 2003, vol. 123, No. 6, pp. 2089-2095.
Duerig et al., "An Overview of Nitinol Medical Applications," Materials Science Engineering, 1999, pp. 149-160; vol. A273.
European Search Report in European Patent Application No. 05799883.3, dated May 10, 2011, in 4 pages.
Extended European Search Report in European Patent Application No. 07753903.9, dated Oct. 8, 2012, in 7 pages.
Extended European Search Report in European Patent Application No. 13813687.4, dated Feb. 24, 2016, in 6 pages.
Extended European Search Report in European Patent Application No. 13813867.2, dated Feb. 26, 2016, in 6 pages.
Extended European Search Report in European Patent Application No. 14779928.2, dated Oct. 7, 2016, in 6 pages.
Federal and Drug Administration 510(k) Summary for Predicate Device IMPELLA 2.5 (K112892), prepared Sep. 5, 2012.
Grech, "Percutaneous Coronary Intervention. I: History and Development," BMJ., May 17, 2003, pp. 1080-1082, vol. 326.
Hsu et al., "Review of Recent Patents on Foldable Ventricular Assist Devices," Recent Patents on Biomedical Engineering, 2012, pp. 208-222, vol. 5.
Ide et al., "Evaluation of the Pulsatility of a New Pulsatile Left Ventricular Assist Device—the Integrated Cardioassist Catheter—in Dogs," J. of Thorac and Cardiovasc Sur, Feb. 1994, pp. 569-0575, vol. 107(2).
Ide et al., "Hemodynamic Evaluation of a New Left Ventricular Assist Device: An Integrated Cardioassist Catheter as a Pulsatile Left Ventricle-Femoral Artery Bypass," Blackwell Scientific Publications, Inc., 1992, pp. 286-290, vol. 16(3).
Impella CP®—Instructions for Use & Clinical Reference Manual (United States only), Abiomed, Inc., Jul. 2014, 148 pages, www.abiomed.com.
Impella LD® with the Impella® Controller—Circulatory Support System—Instructions for Use & Clinical Reference Manual (United States only), Abiomed, Inc., Sep. 2010, 132 pages, www.abiomed.com.
International Preliminary Examination Report in International Patent Application No. PCT/US2003/04853, dated Jul. 26, 2004, in 5 pages.
International Preliminary Examination Report in International Patent Application No. PCT/US2003/04401, dated May 18, 2004, in 4 pages.
International Preliminary Report on Patentability and Written Opinion of the International Searching Authority in International Patent Application No. PCT/US2005/033416, dated Mar. 20, 2007, in 7 pages.
International Preliminary Report on Patentability and Written Opinion of the International Searching Authority in International Patent Application No. PCT/US2007/007313, dated Sep. 23, 2008, in 6 pages.
International Preliminary Report on Patentability and Written Opinion in International Patent Application No. PCT/US2014/020878, dated Sep. 15, 2015, in 8 pages.
International Search Report and Written Opinion in International Patent Application No. PCT/US2005/033416, dated Dec. 11, 2006, in 8 pages.
International Search Report and Written Opinion in International Patent Application No. PCT/US2007/007313, dated Mar. 4, 2008, in 6 pages.

(56) References Cited

OTHER PUBLICATIONS

International Search Report and Written Opinion in International Patent Application No. PCT/US2012/020382, dated Jul. 31, 2012, in 11 pages.
International Search Report and Written Opinion in International Patent Application No. PCT/US2012/020369, dated Jul. 30, 2012, in 10 pages.
International Search Report and Written Opinion in International Patent Application No. PCT/US2012/020553, dated Aug. 17, 2012, in 8 pages.
International Search Report and Written Opinion in International Patent Application No. PCT/US2012/020383, dated Aug. 17, 2012; in 9 pages.
International Search Report and Written Opinion in International Patent Application No. PCT/US2013/040798, dated Aug. 21, 2013, in 16 pages.
International Search Report and Written Opinion in International Patent Application No. PCT/US2013/040799, dated Aug. 21, 2013, in 19 pages.
International Search Report and Written Opinion in International Patent Application No. PCT/US2013/040809, dated Sep. 2, 2013, in 25 pages.
International Search Report and Written Opinion in International Patent Application No. PCT/US2013/048332, dated Oct. 16, 2013, in 17 pages.
International Search Report and Written Opinion in International Patent Application No. PCT/US2013/048343, dated Oct. 11, 2013, in 15 pages.
International Search Report and Written Opinion in International Patent Application No. PCT/US2014/020878, dated May 7, 2014, in 13 pages.
International Search Reort and Written Opinion in International Patent Application No. PCT/US2015/026013, dated Jul. 8, 2015, in 12 pages.
International Search Report and Written Opinion in International Patent Application No. PCT/US2015/026014, dated Jul. 15, 2015, in 13 pages.
International Search Report and Written Opinion in International Patent Application No. PCT/US2015/026025, dated Jul. 20, 2015, in 12 pages.
International Search Report and Written Opinion in International Patent Application No. PCT/US2015/025959, dated Aug. 28, 2015, in 16 pages.
International Search Report and Written Opinion in International Patent Application No. PCT/US2015/025960, dated Sep. 3, 2015, in 15 pages.
International Search Report and Written Opinion in International Patent Application No. PCT/US2015/045370, dated Nov. 18, 2015, in 12 pages.
International Search Report and Written Opinion in International Patent Application No. PCT/US2016/014371, dated May 2, 2016, in 18 pages.
International Search Report and Written Opinion in International Patent Application No. PCT/US2016/014379, dated Jul. 25, 2016, in 19 pages.
International Search Report and Written Opinion in International Patent Application No. PCT/US2016/014391, dated May 2, 2016, in 17 pages.
International Search Report in International Patent Application No. PCT/US2003/004401, dated Nov. 10, 2003, in 9 pages.
International Search Report in International Patent Application No. PCT/US2003/004853, dated Jul. 3, 2003, in 3 pages.
International Search Report Written Opinion in International Patent Application No. PCT/US2010/040847, dated Dec. 14, 2010, in 17 pages.
JOMED Reitan Catheter Pump RCP, Percutaneous Circulatory Support, in 10 pages, believed to be published prior to Oct. 15, 2003.
JOMED Reitan Catheter Pump RCP, Feb. 18, 2003, in 4 pages.

Krishnamani et al., "Emerging Ventricular Assist Devices for Long-Term Cardiac Support," National Review, Cardiology, Feb. 2010, pp. 71-76, vol. 7.
Kunst et al., "Integrated unit for programmable control of the 21 F Hemopump and registration of physiological signals," Medical & Biological Engineering & Computing, Nov. 1994, pp. 694-696.
Mihaylov et al., "Development of a New Introduction Technique for the Pulsatile Catheter Pump," Artificial Organs, 1997, pp. 425-427; vol. 21(5).
Mihaylov et al., "Evaluation of the Optimal Driving Mode During Left Ventricular Assist with Pulsatile Catheter Pump in Calves," Artificial Organs, 1999, pp. 1117-1122; vol. 23(12).
Siess et al., "Basic design criteria for rotary blood pumps," H. Masuda, Rotary Blood Pumps, Springer, Japan, 2000, pp. 69-83.
Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.
Siess et al., "From a lab type to a product: A retrospective view on Impella's assist technology," Artificial Organs, 2001, pp. 414-421, vol. 25, No. 5, Blackwell Science, Inc., International Society for Artificial Organs.
Siess et al., "System analysis and development of intravascular rotation pumps for cardiac assist," Dissertation, Shaker Verlag, Aachen, 1999, 39 pages.
Smith et al., "First-In-Man Study of the Reitan Catheter Pump for Circulatory Support in Patients Undergoing High-Risk Percutaneous Coronary Intervention," Catheterization and Cardiovascular Interventions, 2009, pp. 859-865, vol. 73(7).
Sokolowski et al., "Medical Applications of Shape Memory Polymers," Biomed. Mater. 2007, pp. S23-S27, vol. 2.
"Statistical Analysis and Clinical Experience with the Recover® Pump Systems", Impella CardioSystems GmbH, Sep. 2005, 2 sheets.
Stoeckel et al., "Self-Expanding Nitinol Stents—Material and Design Considerations," European Radiology, 2003, in 13 sheets.
Stolinski et al., "The heart-pump interaction: effects of a microaxial blood pump," International Journal of Artificial Organs, 2002, pp. 1082-1088, vol. 25, Issue 11.
Supplemental European Search Report from the European Patent Office in EP Application No. EP 05799883 dated Mar. 19, 2010, 3 pages (033VEP).
Takagaki et al., "A Novel Miniature Ventricular Assist Device for Hemodynamic Support," ASAIO Journal, 2001, pp. 412-416; vol. 47.
Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).
Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.
Verkerke et al., "Numerical Simulation of the PUCA Pump, A Left Ventricular Assist Device," Abstracts of the XIXth ESAO Congress, The International Journal of Artificial Organs, 1992, p. 543, vol. 15(9).
Verkerke et al., "Numerical Simulation of the Pulsating Catheter Pump: A Left Ventricular Assist Device," Artificial Organs, 1999, pp. 924-931, vol. 23(10).
Verkerke et al., "The PUCA Pump: A Left Ventricular Assist Device," Artificial Organs, 1993, pp. 365-368, vol. 17(5).
Wampler et al., "The Sternotomy Hemopump, A Second Generation Intraarterial Ventricular Assist Device," ASAIO Journal, 1993, pp. M218-M223, vol. 39.
Weber et al., "Principles of Impella Cardiac Support," Supplemental to Cardiac Interventions Today, Aug./Sep. 2009.
Written Opinion in International Patent Application No. PCT/US2003/04853, dated Feb. 25, 2004, 5 pages (FORFLOW.001P).
Minimally Invasive Cardiac Assist JOMED Catheter PumpTM, in 6 pages, believed to be published prior to Jun. 16, 1999.

(56) References Cited

OTHER PUBLICATIONS

Morgan, "Medical Shape Memory Alloy Applications—The Market and its Products," Materials Science and Engineering, 2004, pp. 16-23, vol. A 378.
Morsink et al., "Numerical Modelling of Blood Flow Behaviour in the Valved Catheter of the PUCA-Pump, a LVAD," The International Journal of Artificial Organs, 1997, pp. 277-284; vol. 20(5).
Nishimura et al, "The Enabler Cannula Pump: A Novel Circulatory Support System," The International Journal of Artificial Organs, 1999, pp. 317-323; vol. 22(5).
Nullity Action against the owner of the German part DE 50 2007 005 015.6 of European patent EP 2 047 872 B1, dated Jul. 13, 2015, in 61 pages.
Petrini et al., "Biomedical Applications of Shape Memory Alloys," Journal of Metallurgy, 2011, pp. 1-15.
Raess et al., "Impella 2.5," J. Cardiovasc. Transl. Res., 2009, pp. 168-172, vol. 2(2).
Rakhorst et al., "In Vitro Evaluation of the Influence of Pulsatile Intraventricular Pumping on Ventricular Pressure Patterns," Artificial Organs, 1994, pp. 494-499, vol. 18(7).
Reitan, Evaluation of a New Percutaneous Cardiac Assist Device, Department of Cardiology, Faculty of Medicine, Lund University, Sweden, 2002, in 172 pages.
Reitan et al., "Hemodynamic Effects of a New Percutaneous Circulatory Support Device in a Left Ventricular Failure Model," ASAIO Journal, 2003, pp. 731-736, vol. 49.
Reitan et al., "Hydrodynamic Properties of a New Percutaneous Intra-Aortic Axial Flow Pump," ASAIO Journal 2000, pp. 323-328.
Rothman, "The Reitan Catheter Pump: A New Versatile Approach for Hemodynamic Support", London Chest Hospital Barts & The London NHS Trust, Oct. 22-27, 2006 (TCT 2006: Transcatheter Cardiovascular Therapeutics 18th Annual Scientific Symposium, Final Program), in 48 pages.
Schmitz-Rode et al., "An Expandable Percutaneous Catheter Pump for Left Ventricular Support," Journal of the American College of Cardiology, 2005, pp. 1856-1861, vol. 45(11).
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
Sharony et al, "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).
Sharony et al., "Right Heart Support During Off-Pump Coronary Artery Surgery—A Multi-Center Study," The Heart Surgery Forum, 2002, pp. 13-16, vol. 5(1).
SIEβ et al., "Hydraulic refinement of an intraarterial microaxial blood pump", The International Journal of Artificial Organs, 1995, vol. 18, No. 5, pp. 273-285.
Sieβ, "Systemanalyse and Entwicklung intravasaler Rotationspumpen zur Herzunterstützung", Helmholtz-Institut fur Blomedixinische Technik an der RWTH Aachen, Jun. 24, 1998, in 105 pages.
Extended European Search Report in European Patent Application No. 14764392.8, dated Oct. 27, 2016, in 7 pages.
Schmitz-Rode et al., "Axial flow catheter pump for circulatory support," Biomedizinische Technik, 2002, Band 47, Erganzungsband 1, Teil 1, pp. 142-143.

\* cited by examiner

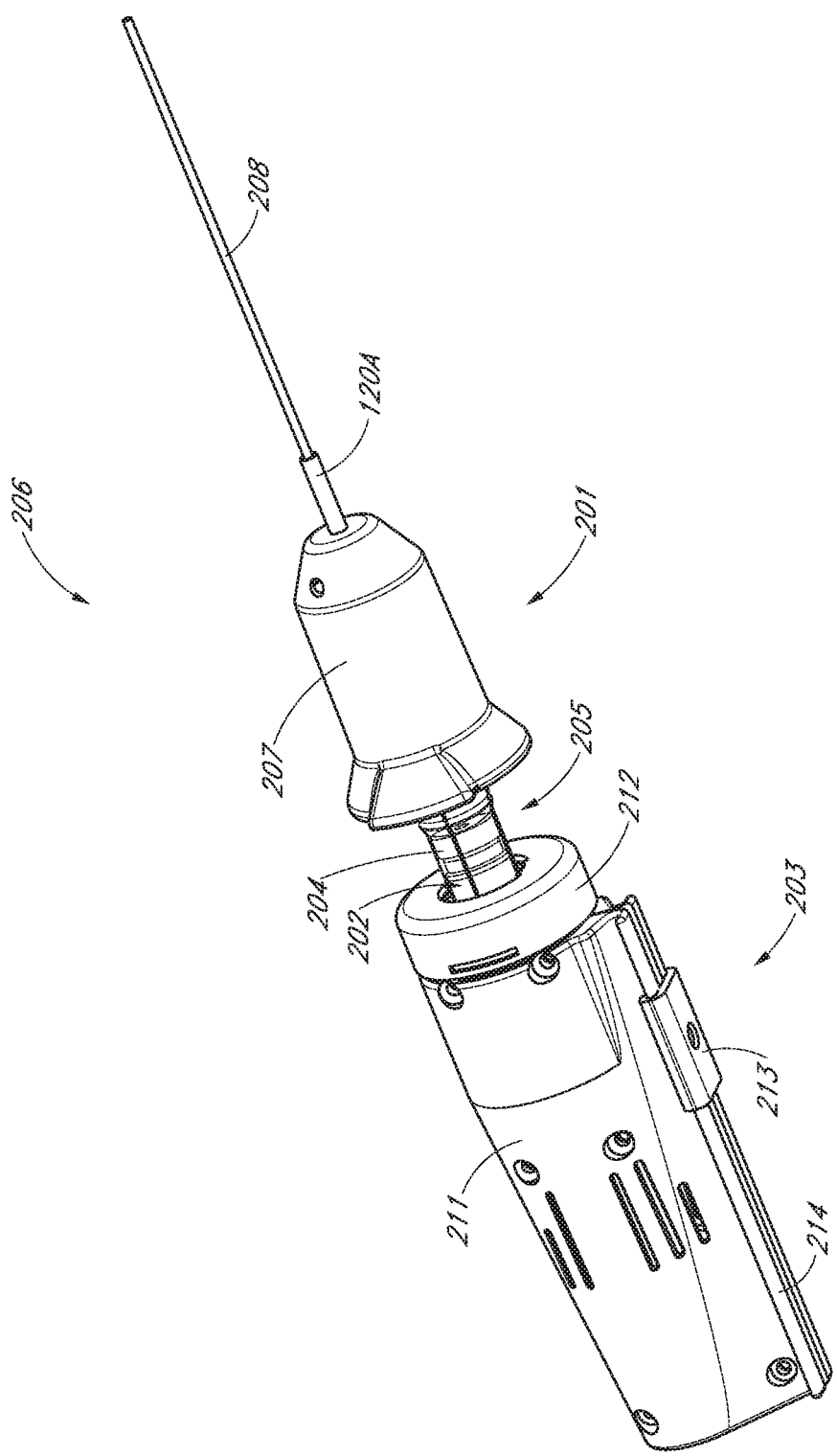

CATHETER PUMP WITH OFF-SET MOTOR POSITION

CROSS-REFERENCE TO RELATED APPLICATIONS

This application claims priority to U.S. Provisional Patent Application No. 61/979,876, filed Apr. 15, 2014, the contents of which are incorporated by reference herein in their entirety and for all purposes.

BACKGROUND OF THE INVENTION

Field of the Invention

This application is directed to heart pumps that can be applied percutaneously and driven extracorporeally with a motor.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently minimally-invasive rotary blood pump have been developed in an attempt to increase the level of potential support (i.e., higher flow). A rotary blood pump is typically inserted into the body and connected to the cardiovascular system, for example, to the left ventricle and the ascending aorta to assist the pumping function of the heart. Other known applications pumping venous blood from the right ventricle to the pulmonary artery for support of the right side of the heart. An aim of acute circulatory support devices is to reduce the load on the heart muscle for a period of time, to stabilize the patient prior to heart transplant or for continuing support.

There is a need for improved mechanical circulatory support devices for treating acute heart failure. Fixed cross-section ventricular assist devices designed to provide near full heart flow rate are either too large to be advanced percutaneously (e.g., through the femoral artery without a cutdown) or provide insufficient flow.

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events. In one aspect, there is a need for a heart pump that can be placed minimally-invasively, for example, through a 15FR or 12FR incision. In one aspect, there is a need for a heart pump that can provide an average flow rate of 4 Lpm or more during operation, for example, at 62 mmHg of head pressure. While the flow rate of a rotary pump can be increased by rotating the impeller faster, higher rotational speeds are known to increase the risk of hemolysis, which can lead to adverse outcomes and in some cases death. Accordingly, in one aspect, there is a need for a pump that can provide sufficient flow at significantly reduced rotational speeds. These and other problems are overcome by the inventions described herein.

Further, there is a need for a motor configured to drive an operative device, e.g., an impeller, at a distal portion of the pump. It can be important for the motor to be configured to allow for percutaneous insertion of the pump's operative device.

SUMMARY OF THE INVENTION

In various embodiments, to provide improved performance as discussed above, a drive shaft or cable is required to operate at a high rotational speed. Such operating conditions may be greatly improved by providing structures that enable more precise rotational positioning of one or more components. Such operating conditions may be greatly improved by providing structures that provide more symmetrical flow of lubricant at least adjacent to or around rotational interfaces including those adjacent to speed or torque transfer members, such as gears, sprockets and other mechanical interface or rotating magnet assemblies or other rotors, such as at the proximal end of the drive shaft.

In one embodiment, a catheter pump assembly is provided that includes an elongate body, an elongate flexible shaft, and an impeller. The elongate body has a proximal end, a distal end and at least one lumen extending therebetween. The elongate flexible shaft has a proximal end and a distal end. The elongate flexible shaft extends through the lumen. The impeller is coupled with the distal end of the elongate flexible shaft. The catheter pump assembly also includes a driven component, a motor, and a tension member. The driven component is coupled with the elongate flexible member. The tension member is coupled with the motor and with the driven component to cause the driven component to rotate when the motor rotates and thereby to cause the elongate flexible shaft and the impeller to rotate.

In one embodiment, a catheter pump assembly is provided that includes a catheter assembly and a drive system. The catheter assembly includes an elongate body, an elongate flexible shaft, and an impeller. The elongate body has a proximal end and a distal end and at least one lumen extending therebetween. The elongate flexible shaft extends through the lumen. The elongate flexible shaft has a proximal end and a distal end. The impeller is coupled with the distal end of the elongate flexible shaft. The catheter assembly includes a first transmission housing disposed at the proximal end of the elongate body. A driven component is journaled in the first transmission housing. The driven component is coupled with the proximal end of the elongate flexible shaft. The drive system includes a second transmission housing, a drive component, a motor and a tension member. The second transmission housing has an enclosed space therein and an open end configured to receive the first transmission housing. The drive component is journaled in the second transmission housing and is configured to engage the driven component when the first transmission housing is received in the open end of the second transmission housing. The tension member is coupled with the motor and extends within the second transmission housing to engage the drive component and to cause the drive component to rotate, and thereby to cause the driven component to rotate.

In another embodiment, a catheter pump assembly is provided that includes a catheter assembly, an operating fluid system, and a drive system. The catheter assembly has an elongate body, an elongate flexible shaft, an impeller, and a driven component. The elongate body has a proximal end and a distal end, a first lumen and a second lumen extending between the proximal and distal ends. The elongate flexible shaft has a proximal end and a distal end and extends through the first lumen. The impeller is disposed distal of the distal end of the elongate flexible shaft. The driven component is coupled with the proximal end of the elongate flexible shaft and is supported for rotation adjacent to the proximal end of the elongate body. An outflow port is disposed proximal of the driven component. The operating fluid system includes a source of operating fluid in communication with the second lumen of the elongate body. The operating fluid is flowable into the second lumen and distally within the elongate body and thereafter proximally in the first lumen to cool and/or lubricate the elongate flexible drive shaft and the driven component. The operating fluid may be referred to herein as an infusate or an infusant. The drive system has a motor and a transmission for transferring torque to the driven component. The motor is disposed laterally of the outflow port such that the operating fluid can be removed from the catheter assembly through the outflow port proximally of the driven component without flowing through the motor.

In another embodiment, a catheter pump assembly is provided that includes an elongate flexible shaft and a transmission housing. The elongate flexible shaft extends through a lumen of a catheter body. An impeller is disposed distal of a distal end of the elongate flexible shaft. A driven component is coupled with the proximal end of the elongate flexible shaft and is supported for rotation relative to the catheter body. The transmission housing has a follower shaft disposed therein. The follower shaft has a proximal end and a distal end. The follower shaft is supported by a bearing at each of the proximal and distal ends thereof. A drive component is mounted on the follower shaft adjacent to the distal end thereof. A speed and torque transfer member is mounted adjacent to the proximal end of the follower shaft. The speed and torque transfer member is configured to transfer a torque applied thereto to the follower shaft and thereby to the drive component and thereby to the driven component to rotate the elongate flexible shaft and the impeller.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 5 is a three dimensional (3D) perspective view of a drive assembly as the drive assembly is being coupled to a driven assembly;

More detailed descriptions of various embodiments of components for heart pumps useful to treat patients experiencing cardiac stress, including acute heart failure, are set forth below.

DETAILED DESCRIPTION

Figure 1:
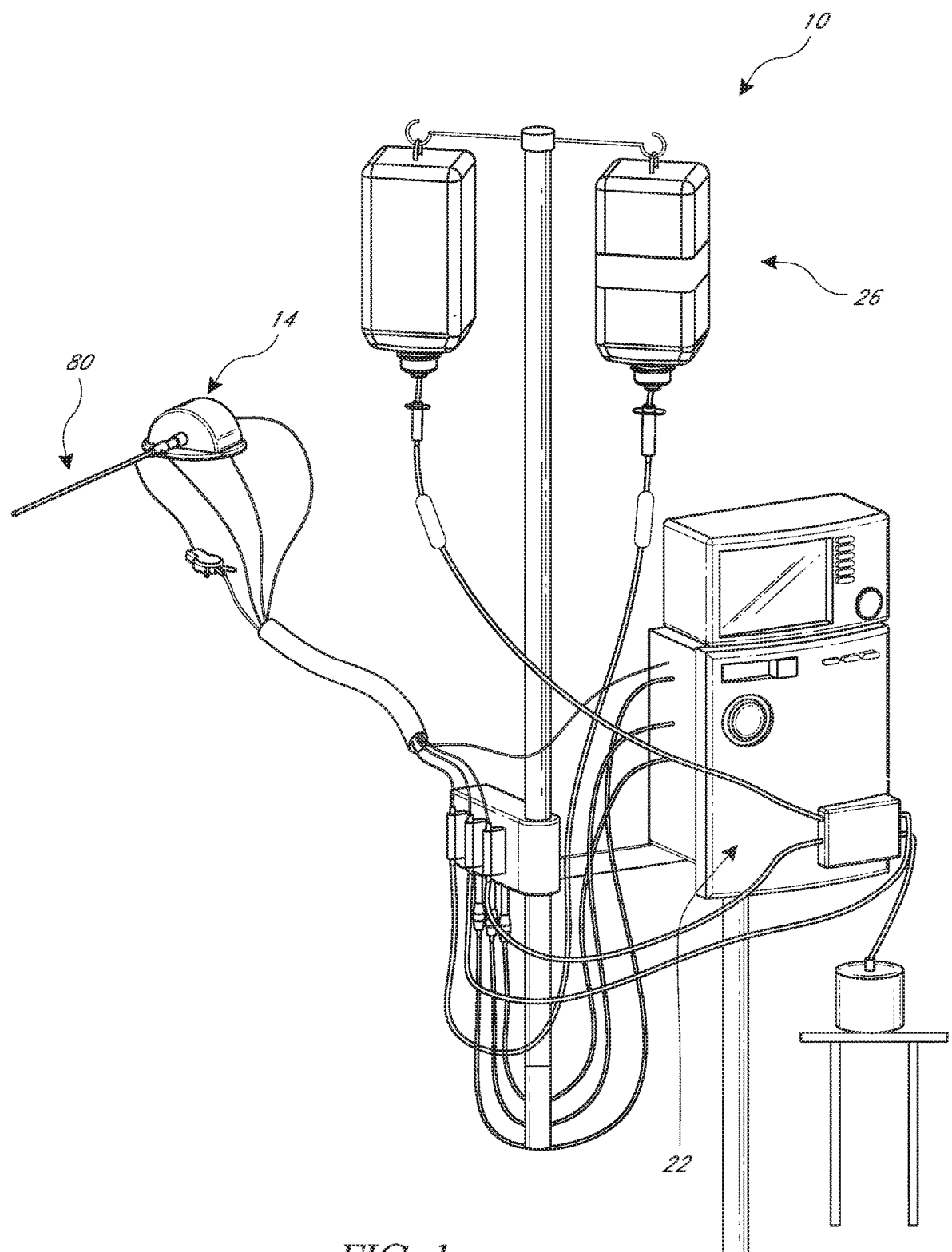
FIG. 1 illustrates one embodiment of a catheter pump configured for percutaneous application and operation.
Figure 2:
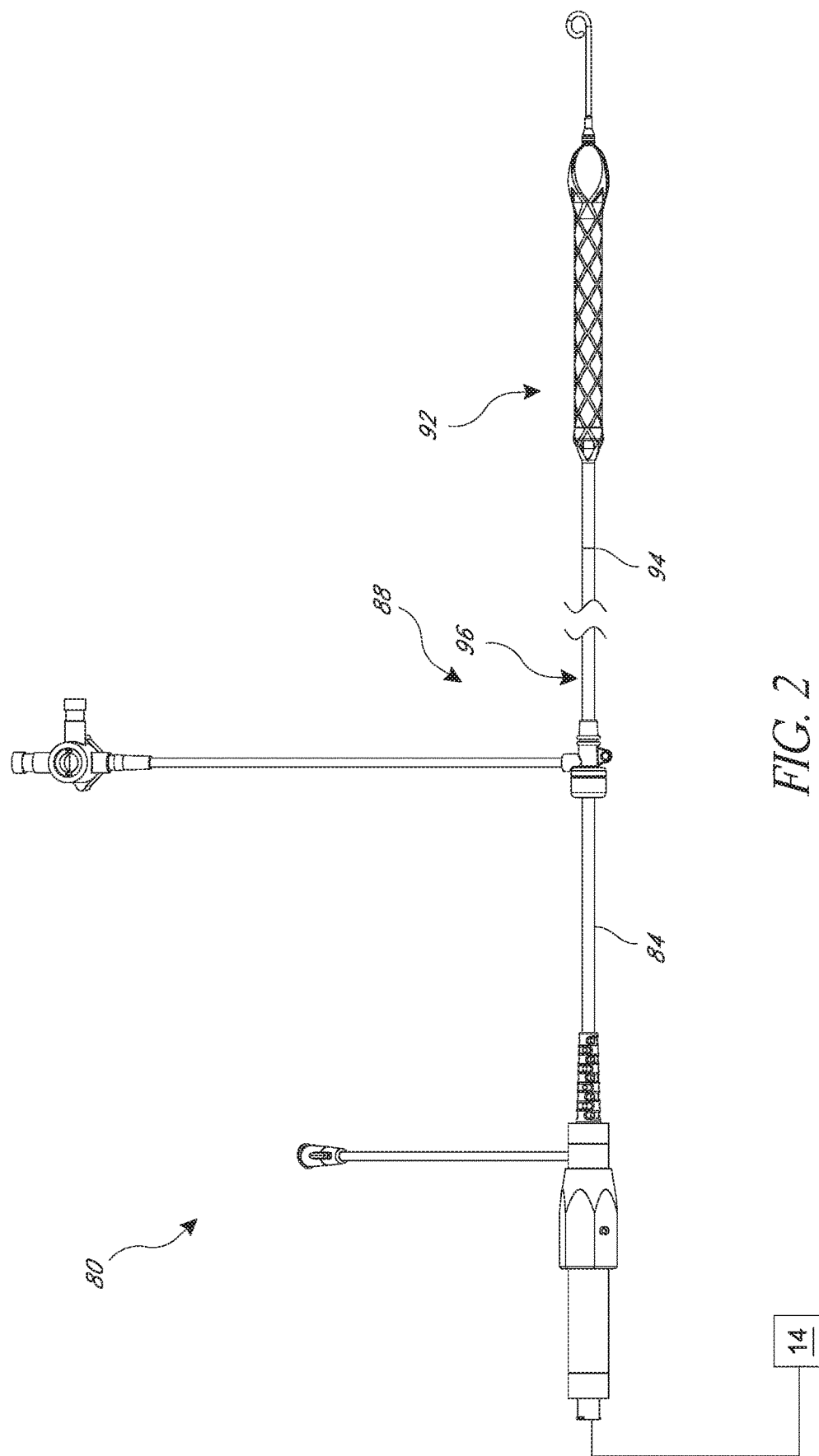
FIG. 2 is a plan view of one embodiment of a catheter adapted to be used with the catheter pump of FIG. 1.
Figure 3:
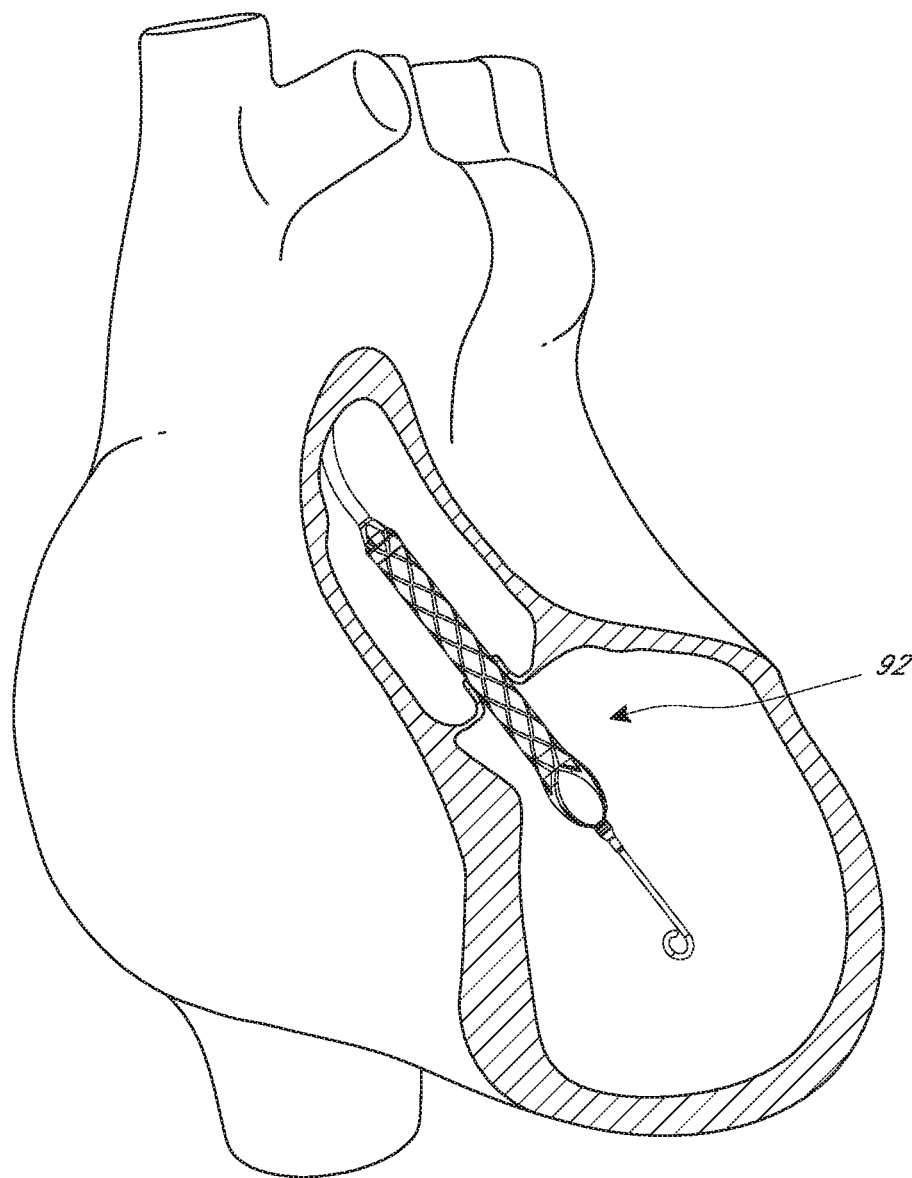
FIG. 3 show a distal portion of the catheter system similar to that of FIG. 2 in position within the anatomy.

This application is directed to apparatuses for inducing motion of a fluid relative to the apparatus. For example, an operative device, such as an impeller, can be coupled at a distal portion of the apparatus. In particular, the disclosed embodiments generally relate to various configurations for a motor adapted to drive an impeller at a distal end of a catheter pump, e.g., a percutaneous heart pump. The disclosed motor assembly may be disposed outside the patient in some embodiments. In other embodiments, the disclosed motor assembly can be miniaturized and sized to be inserted within the body. FIGS. 1-3 show aspects of a catheter pump 10 that can provide high performance flow rates. The pump 10 includes a motor driven by a controller 22. The controller 22 directs the operation of the motor 14 and an infusion or operating fluid system 26 that supplies a flow of operating fluid or infusate in the pump 10.

A catheter system 80 that can be coupled with the motor 14 houses an impeller within a distal portion thereof. In various embodiments, the impeller is rotated remotely by the motor 14 when the pump 10 is operating. For example, the motor 14 can be disposed outside the patient. In some embodiments, the motor 14 is separate from the controller 22, e.g., to be placed closer to the patient. In other embodiments, the motor 14 is part of the controller 22. In other embodiments, the controller 22 is integrated into a patient-adjacent motor assembly 14. In still other embodiments, the motor is miniaturized to be insertable into the patient. Such embodiments allow a shaft conveying torque to an impeller or other operating element at the distal end to be much shorter, e.g., shorter than the distance from the aortic valve to the aortic arch (about 5 cm or less). Some examples of miniaturized motors catheter pumps and related components and methods are discussed in U.S. Pat. Nos. 5,964,694; 6,007,478; 6,178,922; and 6,176,848, all of which are hereby incorporated by reference herein in their entirety for all purposes. Various embodiments of a motor are disclosed herein, including embodiments having separate drive and driven assemblies to enable the use of a guidewire guide passing through the catheter pump. As explained herein, a guidewire guide can facilitate passing a guidewire through the catheter pump for percutaneous delivery of the pump's operative device to a patient's heart. In some embodiments, a motor is separated from a drive component employing a drive belt or other tension member or off-set transmission arrangement. Such further embodiments can improve access to the proximal end of a catheter assembly of the pump 10. Such further embodiments also can improve operation of the rotating components of the pump 10.

FIG. 3 illustrates one use of the catheter pump 10. A distal portion of the pump 10, which can include an impeller assembly 92, is placed in the left ventricle LV of the heart to pump blood from the LV into the aorta. The pump 10 can be used in this way to treat patients with a wide range of conditions, including cardiogenic shock, myocardial infarction, and other cardiac conditions, and also to support a patient during a procedure such as percutaneous coronary intervention. One convenient manner of placement of the distal portion of the pump 10 in the heart is by percutaneous access and delivery using the Seldinger technique or other methods familiar to cardiologists. These approaches enable the pump 10 to be used in emergency medicine, a catheter lab and in other non-surgical settings. Modifications can also enable the pump 10 to support the right side of the heart. Example modifications that could be used for right side support include providing delivery features and/or shaping a distal portion that is to be placed through at least one heart valve from the venous side, such as is discussed in U.S. Pat. Nos. 6,544,216; 7,070,555; and US 2012-0203056A1, all of which are hereby incorporated by reference herein in their entirety for all purposes.

FIG. 2 shows features that facilitate small blood vessel percutaneous delivery and high performance, including up to and in some cases exceeding normal cardiac output in all phases of the cardiac cycle. In particular, the catheter system 80 includes a catheter body 84 and a sheath assembly 88. The catheter body 84 can include an elongate body with proximal and distal end, in which a length of the body 84 enables the pump 10 to be applied to a patient from a peripheral vascular location. The impeller assembly 92 is coupled with the distal end of the catheter body 84. The impeller assembly 92 is expandable and collapsible. In the collapsed state, the distal end of the catheter system 80 can be advanced to the heart, for example, through an artery. In the expanded state the impeller assembly 92 is able to pump blood at high flow rates. FIGS. 2 and 3 illustrate the expanded state. The collapsed state can be provided by advancing a distal end 94 of an elongate body 96 distally over the impeller assembly 92 to cause the impeller assembly 92 to collapse. This provides an outer profile throughout the catheter assembly 80 that is of small diameter, for example, to a catheter size of about 12.5 FR in various arrangements.

In some embodiments, the impeller assembly 92 includes a self-expanding material that facilitates expansion. The catheter body 84 on the other hand preferably is a polymeric body that has high flexibility.

The mechanical components rotatably supporting the impeller within the impeller assembly 92 permit high rotational speeds while controlling heat and particle generation that can come with high speeds. The infusion system 26 delivers a cooling and lubricating solution (sometimes referred to herein as an operating fluid) to the distal portion of the catheter system 80 for these purposes. However, the space for delivery of this fluid is extremely limited. Some of the space is also used for return of the operating fluid. Providing secure connection and reliable routing of operating fluid into and out of the catheter assembly 80 is critical and challenging in view of the small profile of the catheter body 84.

When activated, the catheter pump system can effectively increase the flow of blood out of the heart and through the patient's vascular system. In various embodiments disclosed herein, the pump can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump can be configured to produce an average flow rate at 62 mmHg of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

Various aspects of the pump and associated components are similar to those disclosed in U.S. Pat. Nos. 7,393,181; 8,376,707; 7,841,976; 7,022,100; and 7,998,054, and in U.S. Pub. Nos. 2011/0004046; 2012/0178986; 2012/0172655; 2012/0178985; and 2012/0004495, the entire contents of each of which are incorporated herein for all purposes by reference. In addition, this application incorporates by reference in its entirety and for all purposes the subject matter disclosed in each of the following patent publications: Publication No. 2013/0303970, entitled "DISTAL BEARING SUPPORT," filed on Mar. 13, 2013; Application No. 61/780,656, entitled "FLUID HANDLING SYSTEM," filed on Mar. 13, 2013; Publication No. 2013/0303969, entitled "SHEATH SYSTEM FOR CATHETER PUMP," filed on Mar. 13, 2013; Publication No. 2013/0303830, entitled "IMPELLER FOR CATHETER PUMP," filed on Mar. 13, 2013; and Publication No. 2014/0012065, entitled "CATHETER PUMP," filed on Mar. 13, 2013.

Figure 4:
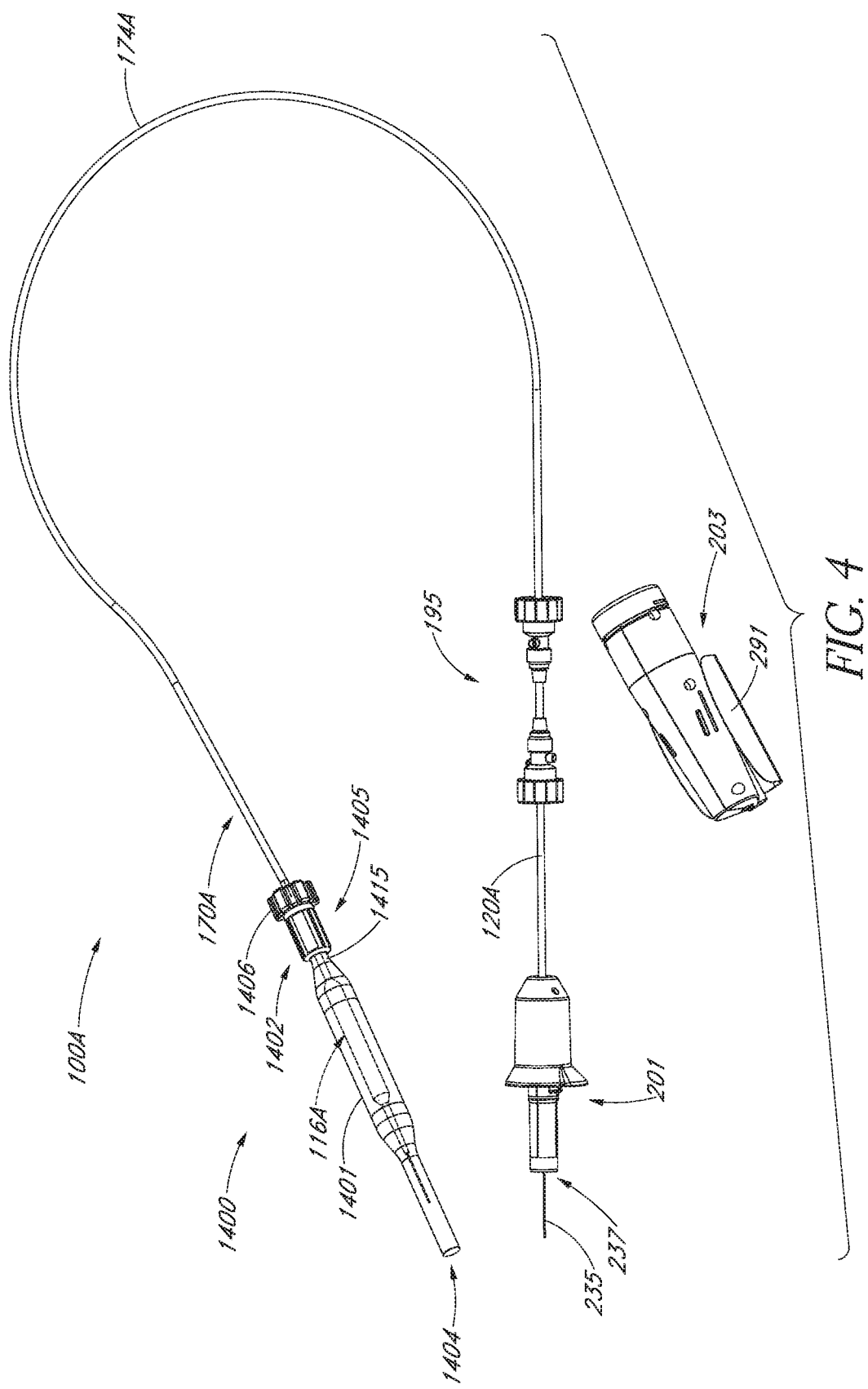
FIG. 4 is a schematic view of a catheter assembly and a drive assembly.

Another example of a catheter assembly 100A is illustrated in FIG. 4. Embodiments of the catheter pump of this application can be configured with a motor that is capable of coupling to (and in some arrangements optionally decoupling from) the catheter assembly 100A. This arrangement provides a number of advantages over a non-disconnectable motor. For example, access can be provided to a proximal end of the catheter assembly 100A prior to or during use. In one configuration, a catheter pump is delivered over a guidewire. The guidewire may be conveniently extended through the entire length of the catheter assembly 100A and out of a proximal portion thereof that is completely enclosed in a coupled configuration. For this approach, connection of the proximal portion of the catheter assembly 100A to a motor housing can be completed after a guidewire has been used to guide the operative device of the catheter pump to a desired location within the patient, e.g., to a chamber of the patient's heart. In other embodiments, discussed below in connection with FIGS. 15-17, a housing enclosing a portion of a motor or drive assembly provides proximal end access to a guidewire lumen or to one or a plurality of ports or conduits for removing fluids from the assembly 100A. In one embodiment, the connection between the motor housing and the catheter assembly is configured to be permanent, such that the catheter assembly, the motor housing and the motor are disposable components. However, in other implementations, the coupling between the motor housing and the catheter assembly is disengageable, such that the motor and motor housing can be decoupled from the catheter assembly after use. In such embodiments, the catheter assembly distal of the motor can be disposable, and the motor and motor housing can be re-usable. One will appreciate from the description herein that the motor can be configured in various manner such that the connection to the rotating shaft can be made within the motor housing or adjacent the housing depending on the application and design parameters. For example, it may be desired to configure the motor so it can be re-used as capital equipment and the catheter is disposable.

Moving from the distal end of the catheter assembly 100A of FIG. 4 to the proximal end, a priming apparatus 1400 can be disposed over an impeller assembly 116A. As explained above, the impeller assembly 116A can include an expandable cannula or housing and an impeller with one or more blades. As the impeller rotates, blood can be pumped proximally (or distally in some implementations) to function as a cardiac assist device.

Figure 4A:
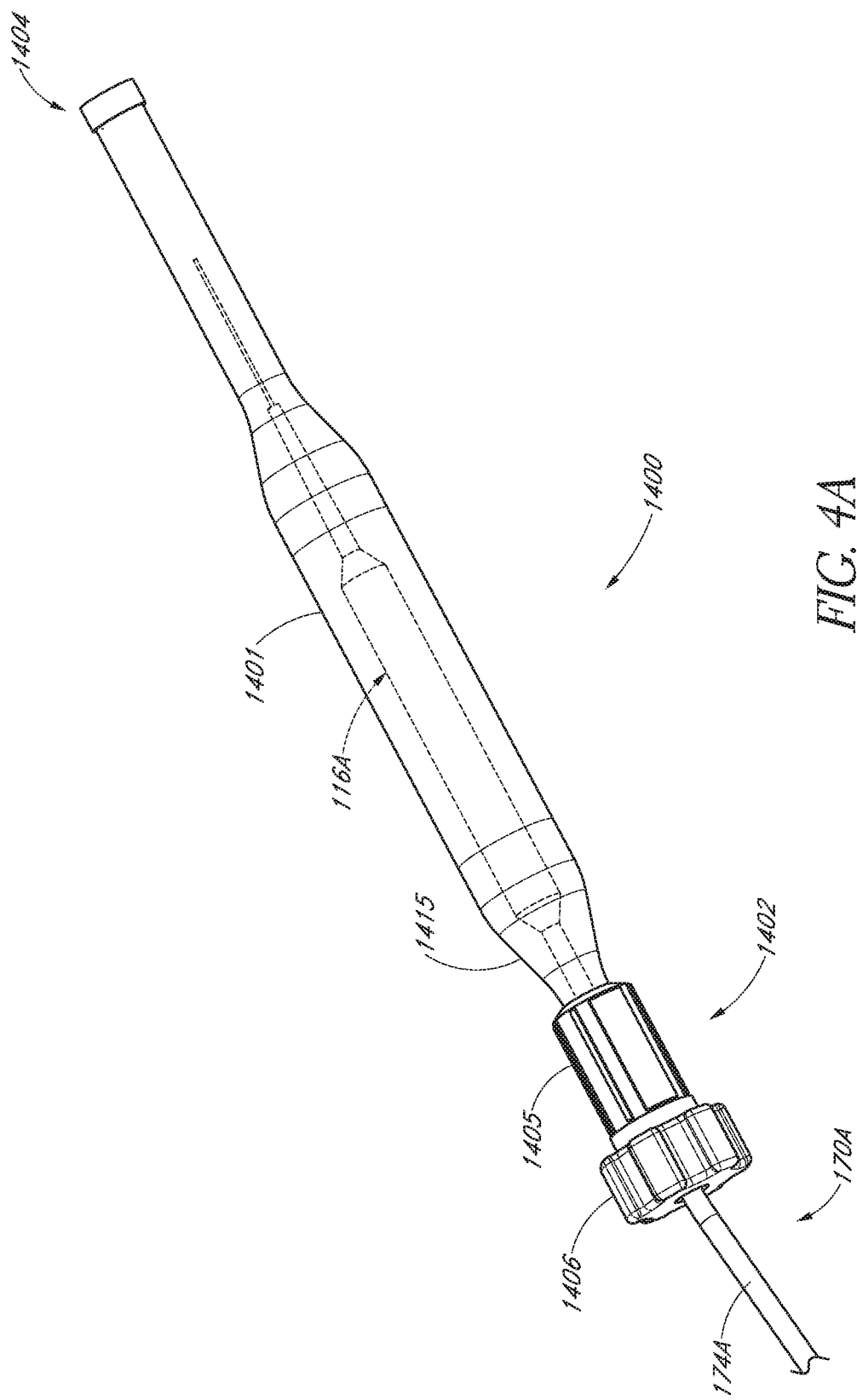
FIG. 4A is an enlarged view of a priming apparatus shown in FIG. 4.

FIG. 4 also shows one example of a priming apparatus 1400 disposed over the impeller assembly 116A near the distal end 170A of the elongate body 174A. FIG. 4A is an enlarged view of the priming apparatus 1400 shown in FIG. 4. The priming apparatus 1400 can be used in connection with a procedure to expel air from the impeller assembly 116A, e.g., any air that is trapped within the housing or that remains within the elongate body 174A near the distal end 170A. For example, the priming procedure may be performed before the pump is inserted into the patient's vascular system, so that air bubbles are not allowed to enter and/or injure the patient. The priming apparatus 1400 can include a primer housing 1401 configured to be disposed around both the elongate body 174A and the impeller assembly 116A. A sealing cap 1406 can be applied to the proximal end 1402 of the primer housing 1401 to substantially seal the priming apparatus 1400 for priming, i.e., so that air does not proximally enter the elongate body 174A and also so that priming fluid does not flow out of the proximal end of the housing 1401. The sealing cap 1406 can couple to the primer housing 1401 in any way known to a skilled artisan. However, in some embodiments, the sealing cap 1406 is threaded onto the primer housing by way of a threaded connector 1405 located at the proximal end 1402 of the primer housing 1401. The sealing cap 1406 can include a sealing recess disposed at the distal end of the sealing cap 1406. The sealing recess can be configured to allow the elongate body 174A to pass through the sealing cap 1406.

The priming operation can proceed by introducing fluid into the sealed priming apparatus 1400 to expel air from the impeller assembly 116A and the elongate body 174A. Fluid can be introduced into the priming apparatus 1400 in a variety of ways. For example, fluid can be introduced distally through the elongate body 174A into the priming apparatus 1400. In other embodiments, an inlet, such as a luer, can optionally be formed on a side of the primer housing 1401 to allow for introduction of fluid into the priming apparatus 1400.

A gas permeable membrane can be disposed on a distal end 1404 of the primer housing 1401. The gas permeable membrane can permit air to escape from the primer housing 1401 during priming.

The priming apparatus 1400 also can advantageously be configured to collapse an expandable portion of the catheter assembly 100A. The primer housing 1401 can include a funnel 1415 where the inner diameter of the housing decreases from distal to proximal. The funnel 1415 may be gently curved such that relative proximal movement of an impeller housing of the impeller assembly 116A causes the impeller housing to be collapsed by the funnel 1415. During or after the impeller housing has been fully collapsed, the distal end 170A of the elongate body 174A can be moved distally relative to the collapsed housing. After the impeller housing is fully collapsed and retracted into the elongate body 174A of the sheath assembly, the catheter assembly 100A can be removed from the priming housing 1400 before a percutaneous heart procedure is performed, e.g., before the pump is activated to pump blood. The embodiments disclosed herein may be implemented such that the total time for infusing the system is minimized or reduced. For example, in some implementations, the time to fully infuse the system can be about six minutes or less. In other implementations, the time to infuse can be about three minutes or less. In yet other implementations, the total time to infuse the system can be about 45 seconds or less. It should be appreciated that lower times to infuse can be advantageous for use with cardiovascular patients.

With continued reference to FIG. 4, the elongate body 174A extends proximally from the impeller assembly 116A to an infusate device 195 configured to allow for infusate to enter the catheter assembly 100A and for waste fluid to leave the catheter assembly 100A. A catheter body 120A (which also passes through the elongate body 174A) can extend proximally and couple to a driven assembly 201. The driven assembly 201 can be configured to receive torque applied by a drive assembly 203, which is shown as being decoupled from the driven assembly 201 and the catheter assembly 100A in FIG. 4. Although not shown in FIG. 4, a drive shaft can extend from the driven assembly 201 through the catheter body 120A to couple to an impeller shaft at or proximal to the impeller assembly 116A. The catheter body 120A can pass within the elongate catheter body 174A such that the external catheter body 174A can axially translate relative to the catheter body 120A.

In addition, FIG. 4 illustrates a guidewire 235 extending from a proximal guidewire opening 237 in the driven assembly 201. Before inserting the catheter assembly 100A into a patient, a clinician may insert the guidewire 235 through the patient's vascular system to the heart to prepare a path for the operative device (e.g., the impeller assembly 116A) to the heart. In some embodiments, the catheter assembly can include a guidewire guide tube (see FIG. 12) passing through a central internal lumen of the catheter assembly 100A from the proximal guidewire opening 237. The guidewire guide tube can be pre-installed in the catheter assembly 100A to provide the clinician with a preformed pathway along which to insert the guidewire 235.

In one approach, a guidewire is first placed in a conventional way, e.g., through a needle into a peripheral blood vessel, and along the path between that blood vessel and the heart and into a heart chamber, e.g., into the left ventricle. Thereafter, a distal end opening of the catheter assembly 100A or guidewire guide tube 312 (discussed below in connection with FIGS. 13 and 14) can be advanced over the proximal end of the guidewire 235 to enable delivery to the catheter assembly 100A. After the proximal end of the guidewire 235 is urged proximally within the catheter assembly 100A and emerges from the guidewire opening 237 and/or guidewire guide, the catheter assembly 100A can be advanced into the patient. In one method, the guidewire guide is withdrawn proximally while holding the catheter assembly 100A. The guidewire guide tube 312 is taken off of the catheter assembly 100A so that guidewire lumens from the proximal end to the distal end of the catheter assembly 100A are directly over the guidewire.

Alternatively, the clinician can thus insert the guidewire 235 through the proximal guidewire opening 237 and urge the guidewire 235 along the guidewire guide tube until the guidewire 235 extends from a distal guidewire opening (not shown) in the distal end of the catheter assembly 100A. The clinician can continue urging the guidewire 235 through the patient's vascular system until the distal end of the guidewire 235 is positioned in the desired chamber of the patient's heart. As shown in FIG. 4, a proximal end portion of the guidewire 235 can extend from the proximal guidewire opening 237. Once the distal end of the guidewire 235 is positioned in the heart, the clinician can maneuver the impeller assembly 116A over the guidewire 235 until the impeller assembly 116A reaches the distal end of the guidewire 235 in the heart. The clinician can remove the guidewire 235 and the guidewire guide tube. The guidewire guide tube can also be removed before or after the guidewire 235 is removed in some implementations.

After removing at least the guidewire 235, the clinician can activate a motor to rotate the impeller and begin operation of the pump.

One problem that arises when using the guidewire 235 to guide the operative device to the heart is that a central lumen or tube (e.g., a guidewire guide) is typically formed to provide a path for the guidewire 235. In some implementations, it may be inconvenient or inoperable to provide a motor or drive assembly having a lumen through which the guidewire 235 can pass. Moreover, in some implementations, it may be desirable to provide the motor or drive assembly separate from the catheter assembly 100A, e.g., for manufacturing or economic purposes. Thus, it can be advantageous to provide a means to couple the drive assembly 203 to the driven assembly 201, while enabling the use of a guidewire guide through which a guidewire may be passed. Preferably, the drive assembly 203 can be securely coupled to the driven assembly 201 such that vibratory, axial, or other external forces do not decouple the drive assembly 203 from the driven assembly 201 during operation. As discussed further below, separating the motor 14 from the driven assembly 201 enhances smooth operation by reducing vibrations in the driven assembly 201 and also provides better access to the proximal end of the catheter assembly 100A. In various implementations, the motor 14 can be laterally offset form the driven assembly 201. Laterally offset includes arrangements where the motor 14 is disposed to the side of a rotational axis of the driven assembly 201. For example, the motor 14 can have an output shaft that rotates about an axis that is parallel to the rotational axis of the driven assembly 201. As another example, a plane perpendicular to and intersecting the output shaft of the motor 14 and/or perpendicular to and intersecting a drive component coupled with the output shaft can intersect a drive component disposed in the driven assembly 201. In other implementations, the motor 14 can be axially spaced form the driven assembly 201. The motor 14 also can be rotationally separate from the driven assembly. These and other similar arrangements are advantageous at least in preventing or reducing the tendency of axial, lateral, vibrational, and other operational forces from being transferred between the motor and the driven assembly 201 or components thereof, specifically from the motor 14 to the driven component 201 and thereby to the working end of the catheter pump 10 and variations thereof. Moreover, the coupling should preferably allow a motor to operate effectively so that the drive shaft is rotated at the desired speed and with the desired torque.

FIG. 5 illustrates one embodiment of a motor assembly 206 as the driven assembly 201 is being coupled to the drive assembly 203. The driven assembly 201 can include a flow diverter 205 and a flow diverter housing 207 that houses the flow diverter 205. The flow diverter 205 can be configured with a plurality of internal cavities, passages, and channels that are configured to route fluid to and from the patient during a medical procedure. As discussed below, an infusate can be directed into the flow diverter from a source of infusate. The infusate is a fluid that flows into the catheter body 120A to provide useful benefits, such as cooling moving parts and keeping blood from entering certain parts of the catheter assembly 100A. The infusate is diverted distally by flow channels in the flow diverter 205. Some of the infusate that flows distally is re-routed back through the catheter body 120A and may be diverted out of the catheter assembly 100A by the flow diverter 205. Moreover, a driven magnet 204 can be disposed within the flow diverter 205 in various embodiments. For example, the driven magnet 204 can be journaled for rotation in a proximal portion of the flow diverter housing 207. The proximal portion can project proximally of a proximal face of a distal portion of the flow diverter housing 207. In other embodiments, the driven magnet 204 can be disposed outside the flow diverter 205. The driven magnet 204 can be configured to rotate freely relative to the flow diverter 205 and/or the flow diverter housing 207. The catheter body 120A can extend from a distal end of the flow diverter housing 207. Further, a drive shaft 208 can pass through the catheter body 120A from the proximal end of the flow diverter housing 207 to the distal end 170A of the elongate body 174A. The drive shaft 208 can be configured to drive the impeller located at the distal end of the catheter assembly 100A. In some embodiments, a distal end of the drive shaft 208 can couple to an impeller shaft, which rotates the impeller.

The drive assembly 203 can include a drive housing 211A or a motor housing 211 having an opening 202 in a cap 212 of the motor housing 211. The motor housing 211 can also have a sliding member 213, which can be configured to couple to the patient's body by way of, e.g., a connector 291 coupled to an adhesive or bandage on the patient's body. Because the motor and motor housing 211 can have a relatively high mass, it can be important to ensure that the motor housing 211 is stably supported. In one implementation, therefore, the motor housing 211 can be supported by the patient's body by way of the sliding member 213 and the connector 291 shown in FIG. 4. The sliding member 213 can slide along a track 214 located on a portion of the motor housing 211, such that relative motion between the motor assembly 206 and the patient does not decouple the sliding member 213 from the patient's body. The sliding member 213 and connector 291 can therefore be configured to provide a structural interface between the motor housing 206 and a platform for supporting the motor housing 211. As explained above, in some arrangements, the platform supporting the motor housing 211 can be the patient, since the motor housing 211 may be positioned quite close to the insertion point. In other arrangements, however, the platform supporting the motor housing 211 may be an external structure.

To couple the drive assembly 203 to the driven assembly 201, the clinician or user can insert the proximal portion of the flow diverter 205 into the opening 202 in the cap 212 of the motor housing 212. After passing through the opening 202, the proximal portion of the flow diverter can reside within a recess formed within the motor housing 211. In some implementations, a securement device is configured to lock or secure the drive assembly 203 to the driven assembly 201 once the driven assembly 201 is fully inserted into the drive assembly 203. In other implementations, the securement device can be configured to secure the drive assembly 203 to the driven assembly 201 by inserting the driven assembly 201 into the drive assembly 203 and then rotating the drive assembly 203 with respect to the driven assembly 201. In some implementations, coupling the drive assembly 203 to the driven assembly 201 may be irreversible, such that there may be no release mechanism to decouple the drive assembly 203 from the driven assembly 201. In implementations without a release mechanism, the catheter assembly 100A (including the driven assembly 201) and the motor housing 211 may be disposable components. In other implementations, however, a release mechanism may be provided to remove the drive assembly 203 from the driven assembly 201. The drive assembly 203 can thereby be used multiple times in some embodiments.

Figure 6:
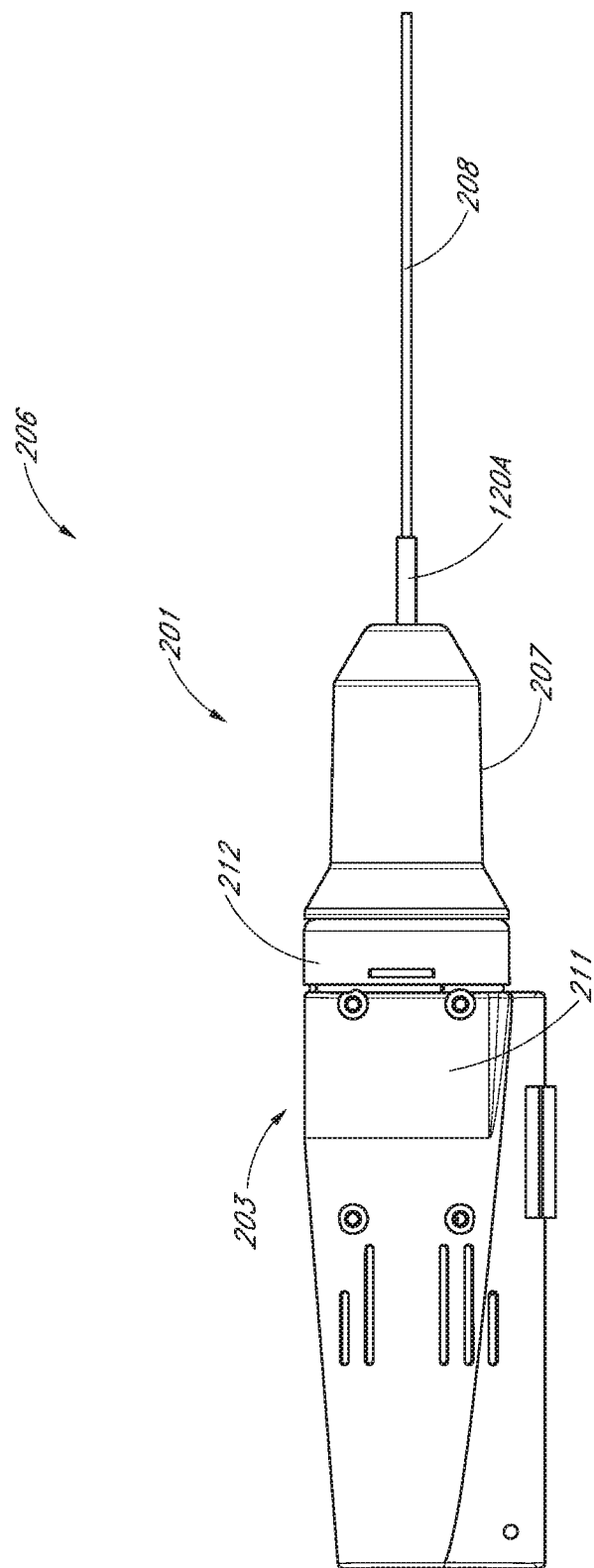
FIG. 6 is a plan view of the drive assembly coupled and secured to the driven assembly.

FIG. 6 illustrates the motor assembly 206 in the assembled state, e.g., after the drive assembly 203 has been secured to the driven assembly 201. When the drive assembly 203 is activated (e.g., a motor is activated to rotate an output shaft), the driven assembly 201, which is operably coupled to the drive assembly, is also activated. The activated driven assembly can cause the drive shaft 208 to rotate, which in turn causes the impeller to rotate to thereby pump blood through the patient.

Figure 7:
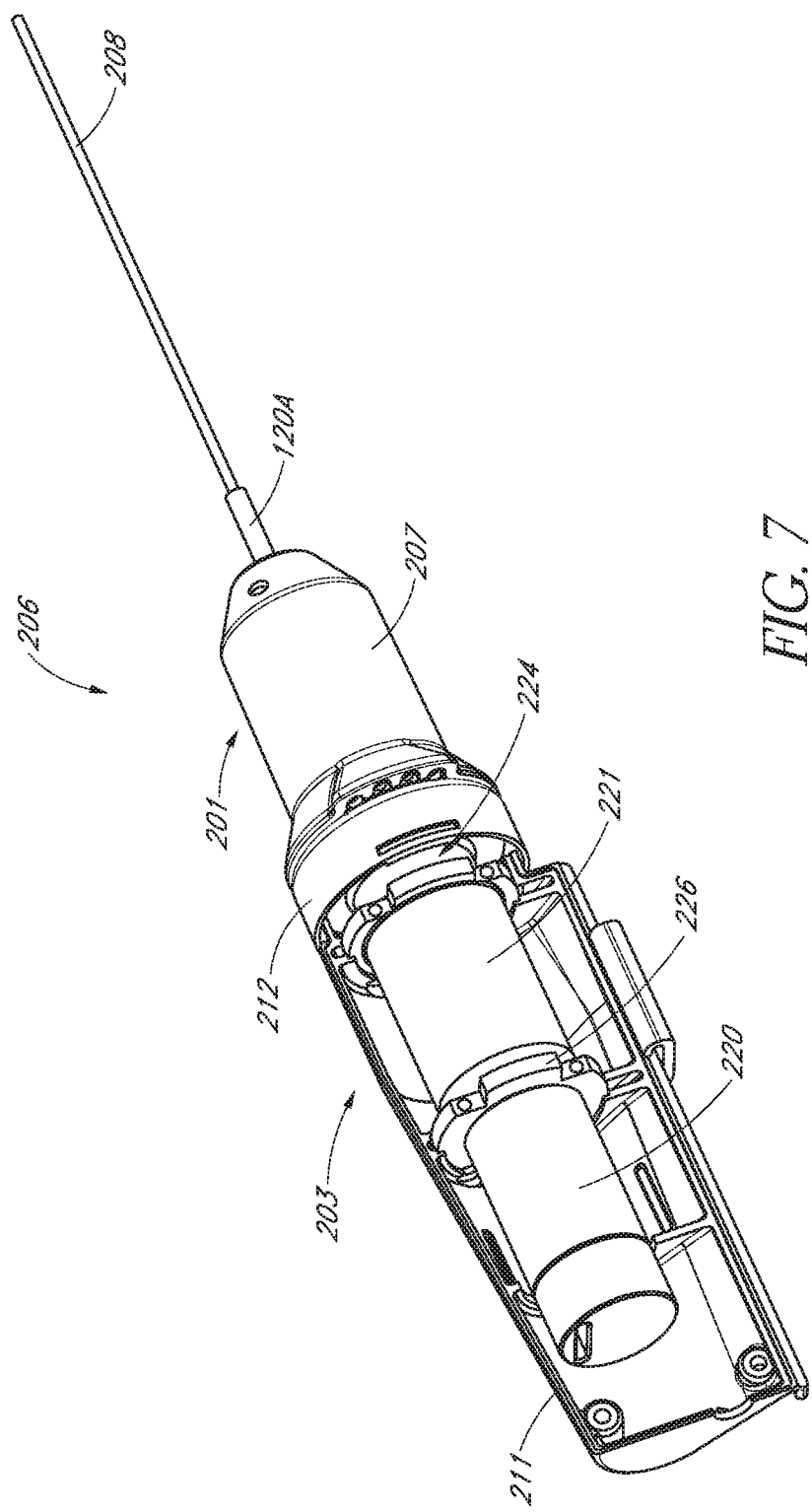
FIG. 7 is a 3D perspective view of a motor assembly including the drive assembly of FIG. 6, wherein various components have been removed for ease of illustration.
Figure 8:
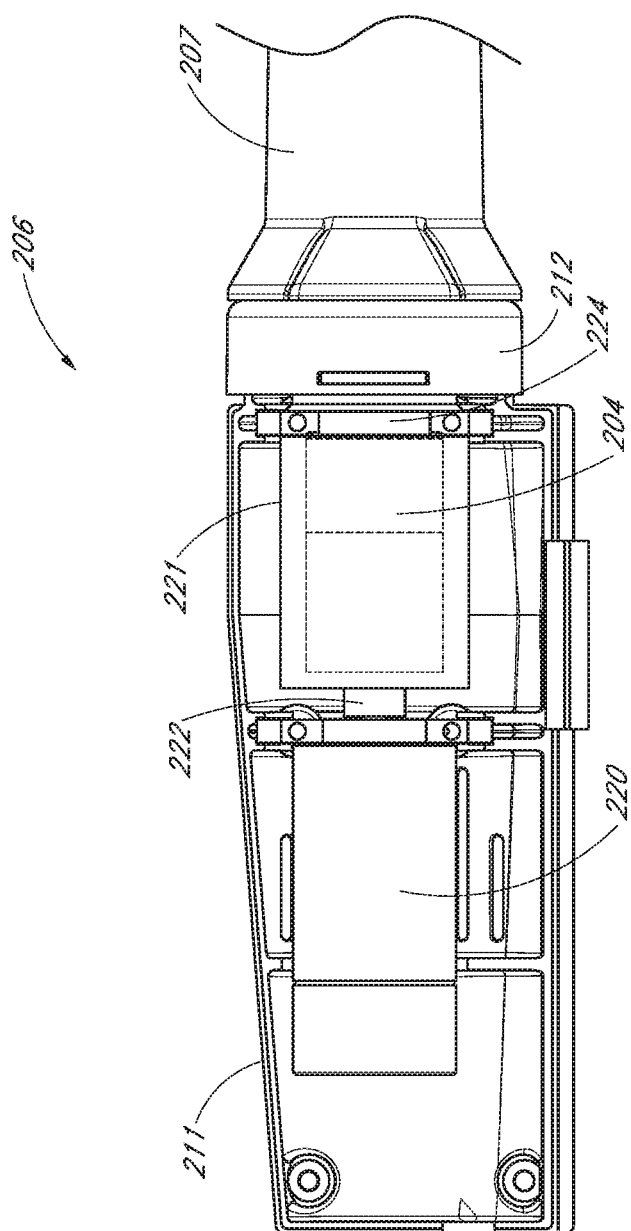
FIG. 8 is a plan view of the motor assembly that illustrates a motor, a drive magnet and a driven magnet.

FIGS. 7-8 illustrate the motor assembly 206 with one wall of the motor housing 211 removed so that various internal components in the housing 211 can be better illustrated. A motor 220 can be positioned within the housing 211 and mounted by way of a motor mount 226. The motor 220 can operably couple to a drive magnet 221. For example, the motor 220 can include an output shaft 222 that rotates the drive magnet 221. In some implementations, the drive magnet 221 can rotate relative to the motor mount 226 and the motor housing 211. Further, in some arrangements, the drive magnet 221 can be free to translate axially between the motor mount and a barrier 224. One advantage of the translating capability is to enable the drive magnet 221 and the driven magnet 204 to self-align by way of axial translation. The barrier 224 can be mounted to the motor housing 211 and at least partially within the cap 212 to support at least the drive magnet 221. In other implementations, the drive assembly 203 can comprise a plurality of motor windings configured to induce rotation of the drive magnet 221. In still other embodiments, motor windings can operate directly on a driven magnet within the driven assembly 201. For example, the windings can be activated in phases to create an electric and/or magnetic field or fields and thereby commutate the driven magnet. Examples of such a configuration are described in U.S. Pat. No. 4,846,152 to Wampler et al. and U.S. Pat. No. 4,895,557 to Moise et al.

Figure 7A:
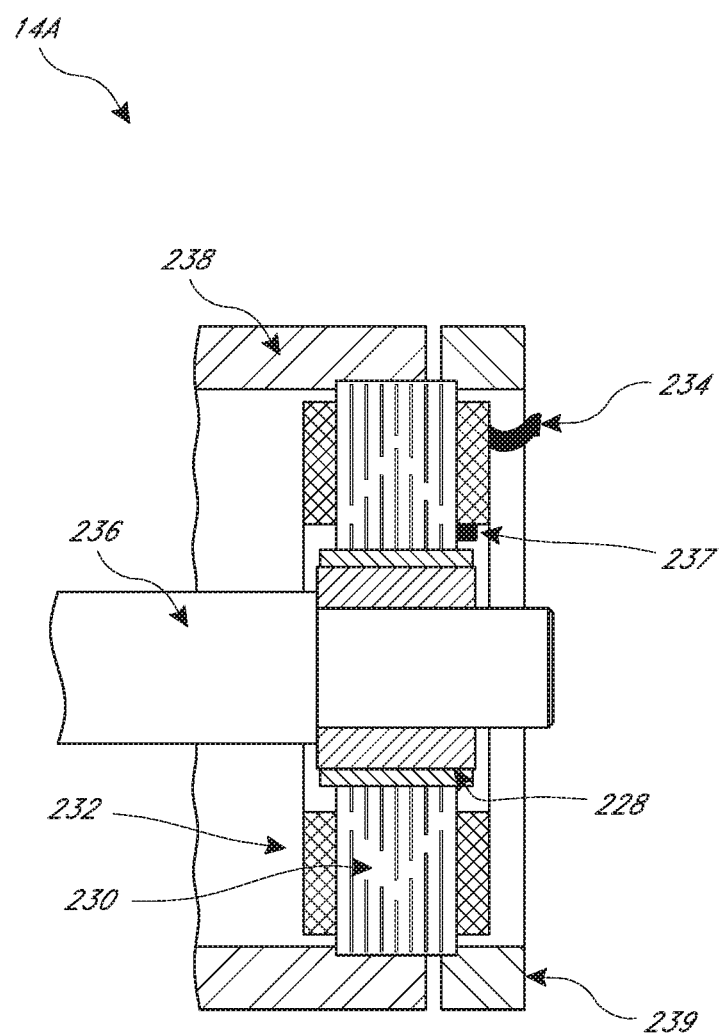
FIG. 7A is a schematic view of another embodiment of a motor assembly that can be used to drive an impeller of a catheter assembly.

FIG. 7A illustrates further details of a frameless motor assembly 14A in which windings are used to induce rotation of a rotor 228. The rotor 228 can include one or more magnets and thus may correspond to the driven magnet 204 or may be coupled with the drive magnet 221. The rotor 228 is positioned within a stator or armature assembly 230. The armature assembly 230 can take any suitable form, such as including a ring-shaped or cylindrical hub in which a plurality of windings 232 are disposed. The windings 232 are coupled by a lead 234 to a control system that is configured (e.g., with one or more processors) to supply the windings 232 with current in an ordered fashion to efficiently energize the windings to drive the rotor 228. The control system can be part of the controller 22. The rotor 228 can be coupled with a shaft 236 to drive the working end of the catheter pump 10. For example, the shaft 236 can be coupled with or can include the proximal end of the drive shaft 208. In another embodiment, the shaft 236 is coupled with a drive component of a transmission including a tension member, as discussed further below in connection with FIGS. 15-17.

The motor assembly 14A can include a sensor 237 that is disposed in the magnetic field of the armature assembly 230 and/or the rotor 228. The sensor 237 can provide feedback to the motor control system, which may be part of the controller 22, to assist in driving the windings of the armature assembly 230. The motor assembly 14A can include a housing 238 in which the armature assembly 230 and rotor 228 are disposed. The housing 238 can include a first recess configured to receive a first portion of the armature assembly 230 and a cap 239 configured to receive a second portion of the armature assembly 230. The housing 238 and cap 239 hold the first and second portions and thereby.

In FIG. 8, the drive magnet 221 is illustrated in phantom, such that the driven magnet 204 can be seen disposed within the drive magnet 221. Although not illustrated, the poles of the drive magnet 221 can be formed on an interior surface of the drive magnet 221, and the poles of the driven magnet 204 can be formed on an exterior surface of the driven magnet 204. As the drive magnet 221 rotates, the poles of the drive magnet 221 can magnetically engage with corresponding, opposite poles of the driven magnet 204 to cause the driven magnet 204 to rotate with, or follow, the drive magnet 221. Because the driven magnet 204 can be mechanically coupled to the drive shaft 208, rotation of the drive magnet 221 can cause the driven magnet 204 and the drive shaft 208 to rotate at a speed determined in part by the speed of the motor 220. Furthermore, when the driven magnet 204 is inserted into the drive magnet 221, the poles of each magnet can cause the drive magnet 221 and the driven magnet 204 to self-align. The magnetic forces between the drive magnet 221 and the driven magnet 204 can assist in coupling the drive assembly 203 to the driven assembly 201.

Figure 9:
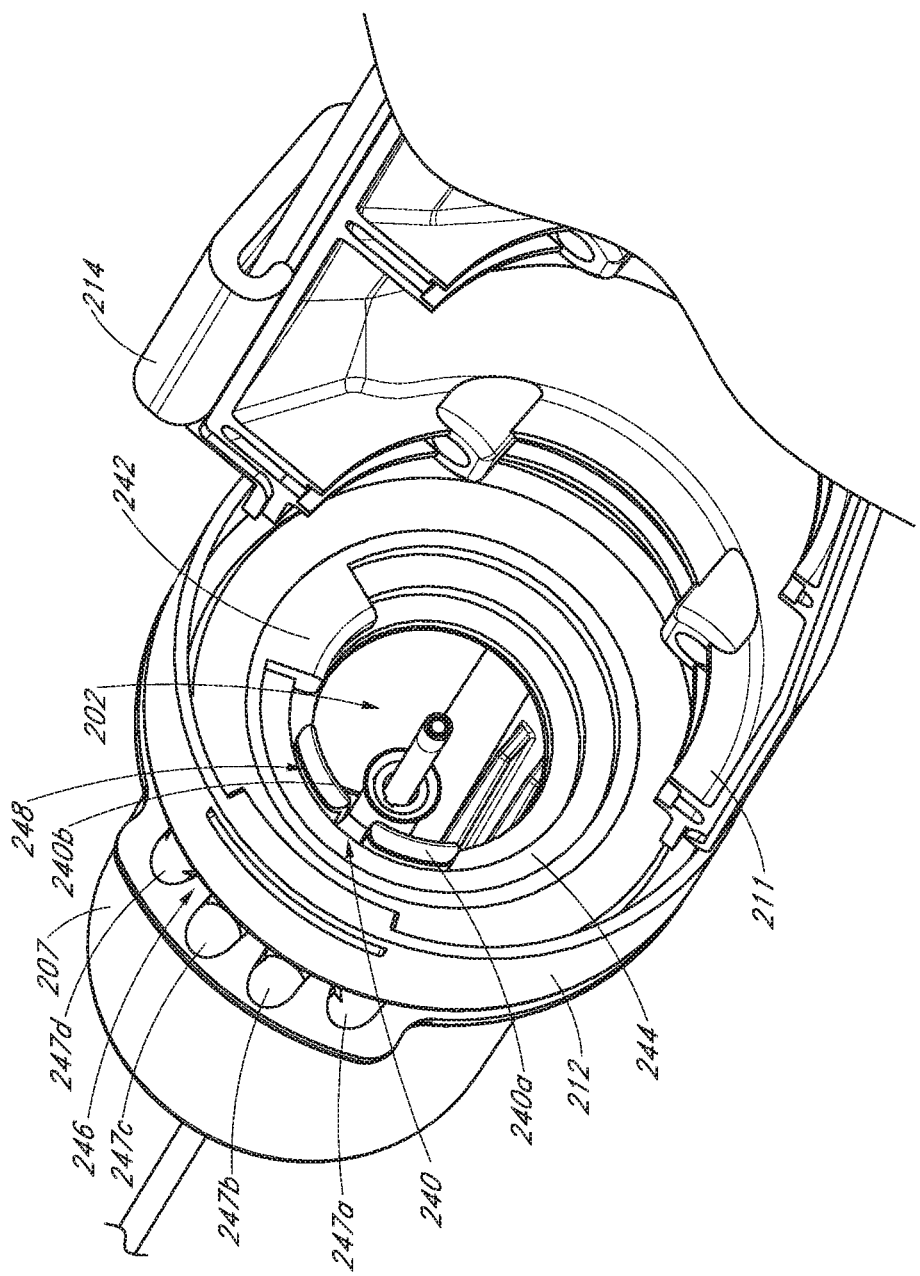
FIG. 9 is a 3D perspective view of a first securement device configured to secure the drive assembly to the driven assembly.

Turning to FIG. 9, a 3D perspective view of various components at the interface between the drive assembly 203 and the driven assembly 201 is shown. Various components have been hidden to facilitate illustration of one means to secure the drive assembly 203 to the driven assembly 201. A first securement device 240 is illustrated in FIG. 9. The first securement device can comprise a first projection 240a and a second projection 240b. Furthermore, a locking recess 244 can be formed in the cap 212 around at least a portion of a perimeter of the opening 202. A lip 242 can also extend from the perimeter at least partially into the opening 202. As shown, the lip 242 can also extend proximally from the locking recess 244 such that a step is formed between the locking recess 244 and the lip 242. Further, a flange 246 can be coupled to or formed integrally with the flow diverter housing 207. In certain embodiments, the flange 246 can include a plurality of apertures 247a, 247b, 247c, 247d that are configured to permit tubes and cables to pass therethrough to fluidly communicate with lumens within the flow diverter 205. In some implementations, three tubes and one electrical cable can pass through the apertures 247a-d. For example, the electrical cable can be configured to electrically couple to a sensor within the catheter assembly 100A, e.g., a pressure sensor. The three tubes can be configured to carry fluid to and from the catheter assembly 100A. For example, a first tube can be configured to carry infusate into the catheter assembly 100A, a second tube can be configured to transport fluids to the pressure sensor region, and the third tube can be configured to transport waste fluid out of the catheter assembly 100A. In other embodiments, one or more fluid passages may provide fluid communication between fluid channels in the catheter assembly 100A and a proximal portion of a transmission or drive component as discussed below in connection with FIGS. 15-17. For example, as discussed below a fluid conduit can be coupled with a proximal port of a shaft in a drive component or transmission to convey waste fluid to a waste container. Although not illustrated, the tubes and cable(s) can pass through the apertures 247a-d of the flange 246 and can rest against the motor housing 211. By organizing the routing of the tubes and cable(s), the apertures 247a-d can advantageously prevent the tubes and cable(s) from becoming entangled with one another or with other components of the catheter pump system.

When the driven assembly 201 is inserted into the opening 202, the first and second projections 240a, 240b can pass through the opening and engage the locking recess 244. In some implementations, the projections 240a, 240b and the locking recess 244 can be sized and shaped such that axial translation of the projections 240a, 240b through the opening 202 causes a flange or tab 248 at a distal end of each projection 240a, 240b to extend over the locking recess 244. Thus, in some embodiments, once the projections 240a, 240b are inserted through the opening 202, the tabs 248 at the distal end of the projections 240a, 240b are biased to deform radially outward to engage the locking recess 244 to secure the driven assembly 201 to the drive assembly 203.

Once the driven assembly 201 is secured to the drive assembly 203, the flow diverter housing 207 can be rotated relative to the motor cap 212. By permitting relative rotation between the driven assembly 201 and the drive assembly 203, the clinician is able to position the impeller assembly 116A within the patient at a desired angle or configuration to achieve the best pumping performance. As shown in FIG. 9, however, the lip 242 can act to restrict the relative rotation between the driven assembly 201 (e.g., the flow diverter housing 207) and the drive assembly 203 (e.g. the cap 212 and the motor housing 211). As illustrated, the flange 246 and apertures 247a-d can be circumferentially aligned with the projections 240a, 240b. Further, the lip 242 can be circumferentially aligned with the sliding member 213, the track 214, and the connector 291 of the motor housing 211. If the flange 246 and projections 240a, 240b are rotated such that they circumferentially align with the lip 242, then the tubes and cable(s) that extend from the apertures 247a-d may become entangled with or otherwise obstructed by the sliding member 213 and the connector 291. Thus, it can be advantageous to ensure that the sliding member 213 and the connector 291 (or any other components on the outer surface of the housing 211) do not interfere or obstruct the tubes and cable(s) extending out of the apertures 247a-d of the flange 246. The lip 242 formed in the cap 212 can act to solve this problem by ensuring that the flange 246 is circumferentially offset from the sliding member 213 and the connector 291.

For example, the flow diverter housing 207 can be rotated until one of the projections 240a, 240b bears against a side of the lip 242. By preventing further rotation beyond the side of the lip 242, the lip 242 can ensure that the flange 246 and apertures 247a-d are circumferentially offset from the sliding member 213, the track 214, and the connector 291.

In one embodiment, once the catheter assembly 100A is secured to the motor housing 211, the connection between the driven assembly 201 and the drive assembly 203 may be configured such that the drive assembly 203 may not be removed from the driven assembly 201. The secure connection between the two assemblies can advantageously ensure that the motor housing 211 is not accidentally disengaged from the catheter assembly 100A during a medical procedure. In such embodiments, both the catheter assembly 100A and the drive assembly 203 may preferably be disposable.

In other embodiments, however, it may be desirable to utilize a re-usable drive assembly 203. In such embodiments, therefore, the drive assembly 203 may be removably engaged with the catheter assembly 100A (e.g., engaged with the driven assembly 201). For example, the lip 242 may be sized and shaped such that when the drive assembly 203 is rotated relative to the driven assembly 201, the tabs 248 are deflected radially inward over the lip 242 such that the driven assembly 201 can be withdrawn from the opening 202. For example, the lip 242 may include a ramped portion along the sides of the lip 242 to urge the projections 240a, 240b radially inward. It should be appreciated that other release mechanisms are possible.

Figure 10A:
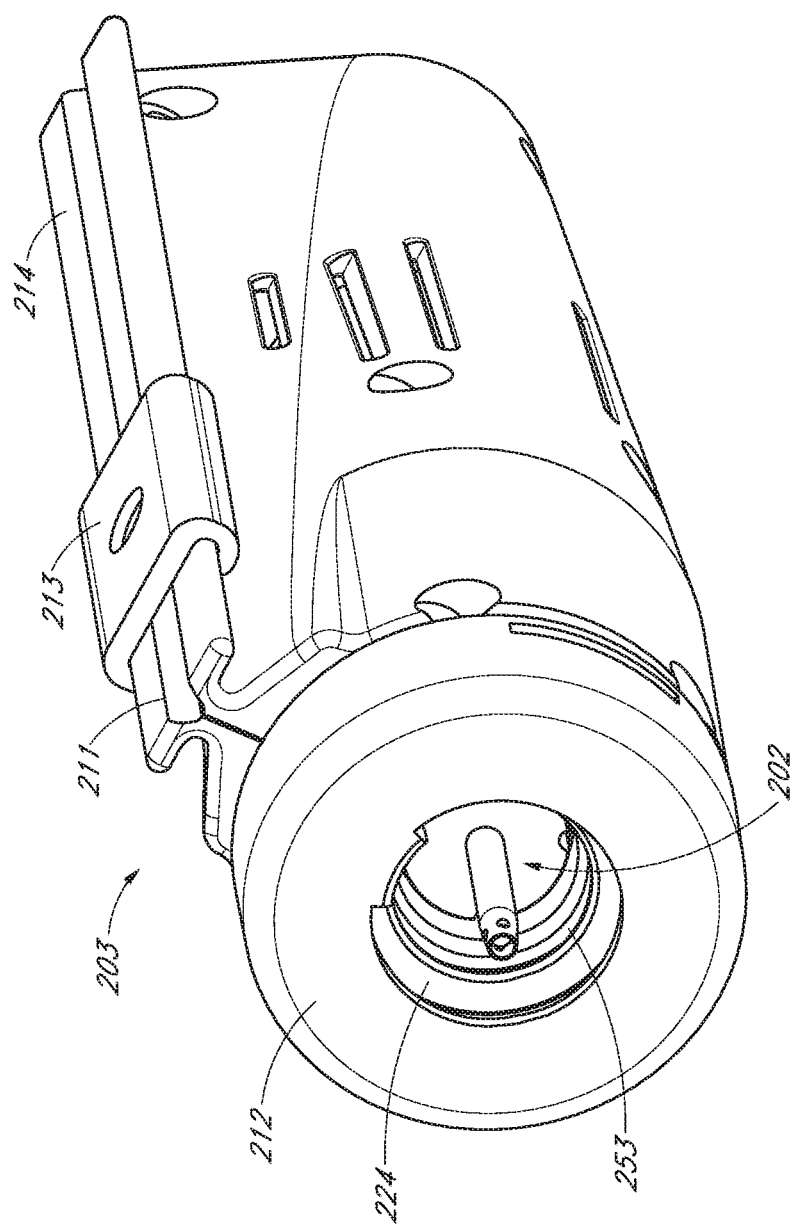
FIGS. 10A-10C are 3D perspective views of a second securement device configured to secure the drive assembly to the driven assembly.
Figure 10B:
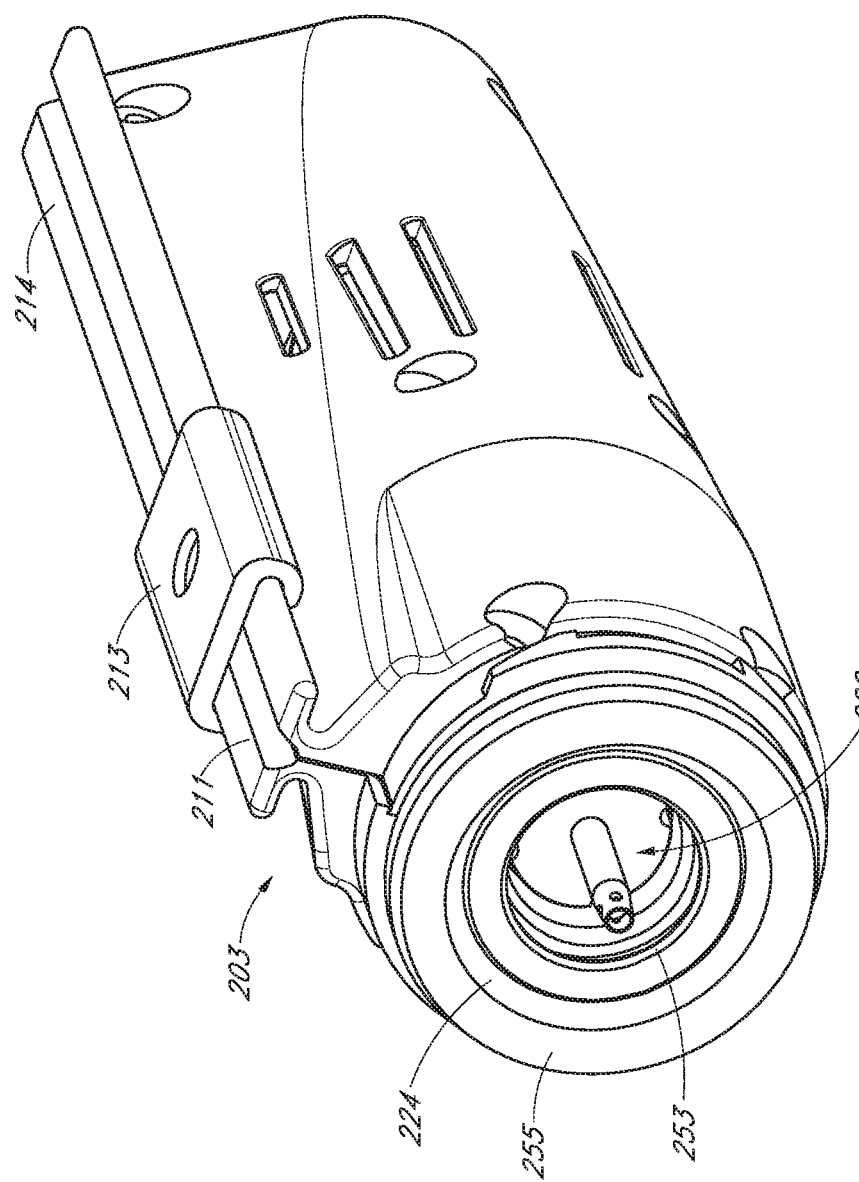
Figure 10C:
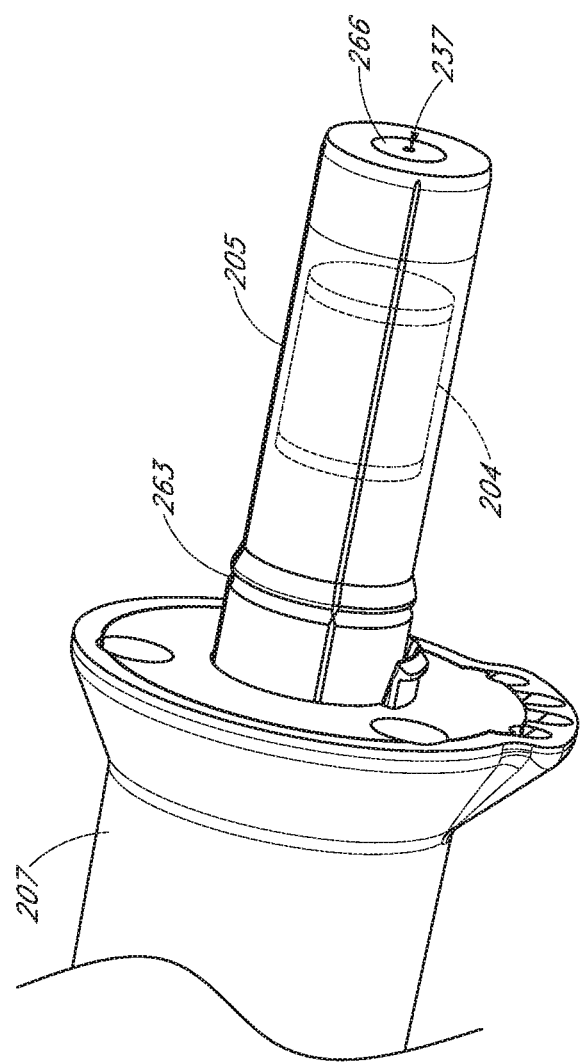

Turning to FIGS. 10A-10C, an additional means to secure the drive assembly 203 to the driven assembly 201 is disclosed. As shown in the 3D perspective view of FIG. 10A, a locking O-ring 253 can be mounted to the barrier 224 that is disposed within the motor housing 211 and at least partially within the cap 212. In particular, the locking O-ring 253 can be mounted on an inner surface of the drive or motor housing 203 surrounding the recess or opening 202 into which the driven assembly 212 can be received As explained below, the locking O-ring can act as a detent mechanism and can be configured to be secured within an arcuate channel formed in an outer surface of the driven assembly 201, e.g., in an outer surface of the flow diverter 205 in some embodiments. In other embodiments, various other mechanisms can act as a detent to secure the driven assembly 201 to the drive assembly 203. For example, in one embodiment, a spring plunger or other type of spring-loaded feature may be cut or molded into the barrier 224, in a manner similar to the locking O-ring 253 of FIGS. 10A-10C. The spring plunger or spring-loaded feature can be configured to engage the arcuate channel, as explained below with respect to FIG. 10C. Skilled artisans will understand that other types of detent mechanisms can be employed.

FIG. 10B illustrates the same 3D perspective of the drive assembly 203 as shown in FIG. 10A, except the cap 212 has been hidden to better illustrate the locking O-ring 253 and a second, stabilizing O-ring 255. The O-ring 255 is an example of a damper that can be provided between the motor 220 and the catheter assembly 100A. The damper can provide a vibration absorbing benefit in some embodiments. In other embodiment, the damper may reduce noise when the pump is operating. The damper can also both absorb vibration and reduce noise in some embodiments. The stabilizing O-ring 255 can be disposed within the cap 212 and can be sized and shaped to fit along the inner recess forming the inner perimeter of the cap 212. The stabilizing O-ring 255 can be configured to stabilize the cap 212 and the motor housing 211 against vibrations induced by operation of the motor 220. For example, as the motor housing 211 and/or cap 212 vibrate, the stabilizing O-ring 255 can absorb the vibrations transmitted through the cap 212. The stabilizing O-ring 255 can support the cap 212 to prevent the cap from deforming or deflecting in response to vibrations. In some implementations, the O-ring 255 can act to dampen the vibrations, which can be significant given the high rotational speeds involved in the exemplary device.

In further embodiments, a damping material can also be applied around the motor 220 to further dampen vibrations. The damping material can be any suitable damping material, e.g., a visco-elastic or elastic polymer. For example, the damping material may be applied between the motor mount 226 and the motor 220 in some embodiments. In addition, the damping material may also be applied around the body of the motor 220 between the motor 220 and the motor housing 211. In some implementations, the damping material may be captured by a rib formed in the motor housing 211. The rib may be formed around the motor 220 in some embodiments.

Turning to FIG. 10C, a proximal end of the driven assembly 201 is shown. As explained above, the flow diverter 205 (or the flow diverter housing in some embodiments) can include an arcuate channel 263 formed in an outer surface of the flow diverter 205. The arcuate channel 263 can be sized and shaped to receive the locking O-ring 253 when the flow diverter 205 is inserted into the opening 202 of the drive assembly 203. As the flow diverter 205 is axially translated through the recess or opening 202, the locking O-ring 253 can be urged or slid over an edge of the channel 263 and can be retained in the arcuate channel 263. Thus, the locking O-ring 253 and the arcuate channel 263 can operate to act as a second securement device. Axial forces applied to the motor assembly 206 can thereby be mechanically resisted, as the walls of the arcuate channel 263 bear against the locking O-ring 253 to prevent the locking O-ring 253 from translating relative to the arcuate channel 263. In various arrangements, other internal locking mechanisms (e.g., within the driven assembly 201 and/or the drive assembly 203) can be provided to secure the driven and drive assemblies 201, 203 together. For example, the driven magnet 204 and the drive magnet 221 may be configured to assist in securing the two assemblies together, in addition to aligning the poles of the magnets. Other internal locking mechanisms may be suitable.

FIG. 10C also illustrates a resealable member 266 disposed within the proximal end portion of the driven assembly 201, e.g., the proximal end of the catheter assembly 100A as shown in FIG. 4. As in FIG. 4, the proximal guidewire opening 237 can be formed in the resealable member 266. As explained above with respect to FIG. 4, the guidewire 235 can be inserted through the proximal guidewire opening 237 and can be maneuvered through the patient's vasculature. After guiding the operative device of the pump to the heart, the guidewire 235 can be removed from the catheter assembly 100A by pulling the guidewire 235 out through the proximal guidewire opening 237. Because fluid may be introduced into the flow diverter 205, it can be advantageous to seal the proximal end of the flow diverter 205 to prevent fluid from leaking out of the catheter assembly 100A. The resealable member 266 can therefore be formed of an elastic, self-sealing material that is capable of closing and sealing the proximal guidewire opening 237 when the guidewire 235 is removed. The resealable member can be formed of any suitable material, such as an elastomeric material. In some implementations, the resealable member 266 can be formed of any suitable polymer, e.g., a silicone or polyisoprene polymer. Skilled artisans will understand that other suitable materials may be used.

Figure 11:
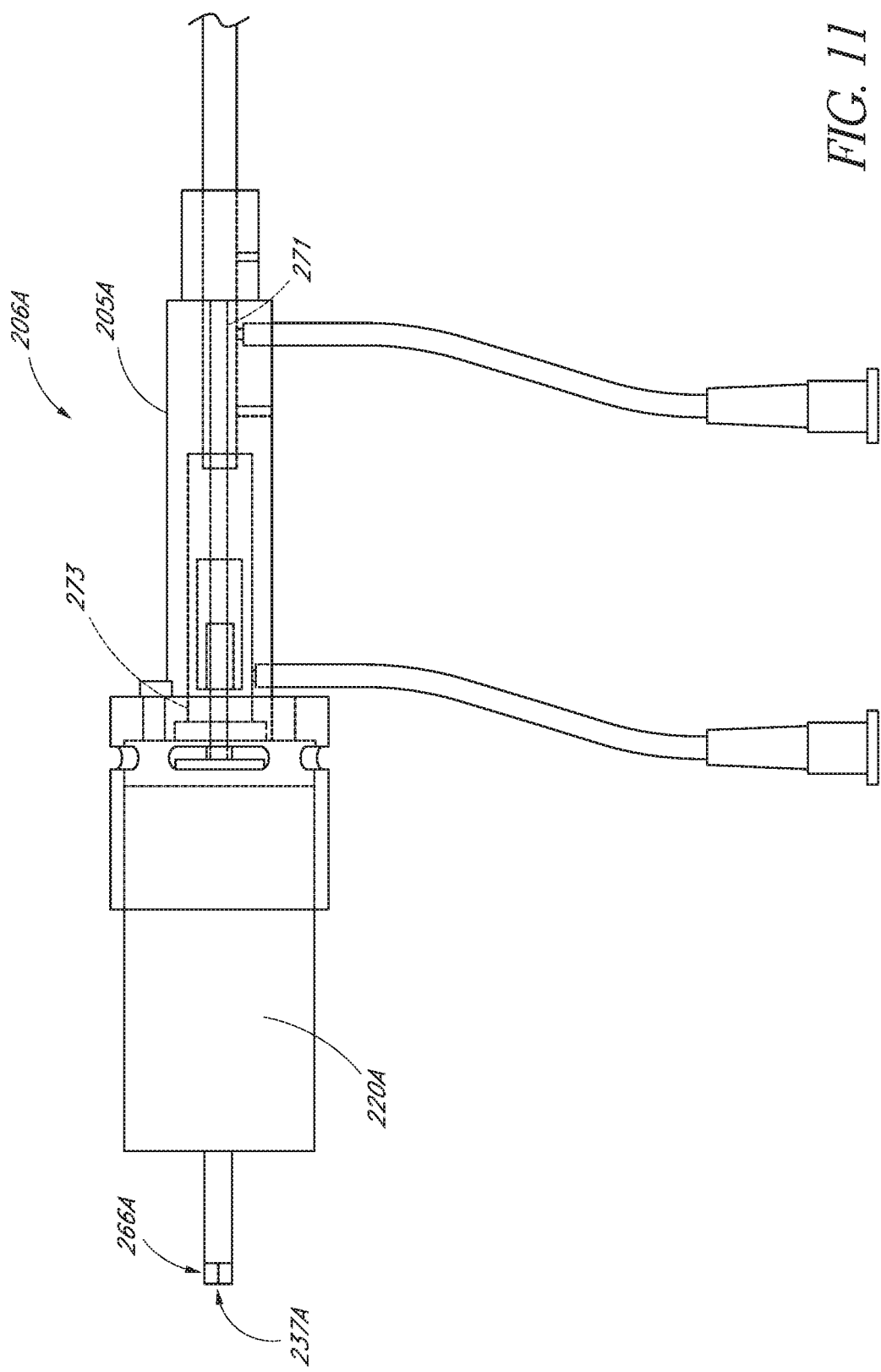
FIG. 11 illustrates a side schematic view of a motor assembly according to another embodiment.

FIG. 11 illustrates yet another embodiment of a motor assembly 206A coupled to a catheter assembly. In FIG. 11, a flow diverter is disposed over and coupled to a catheter body 271 that can include a multi-lumen sheath configured to transport fluids into and away from the catheter assembly. The flow diverter 205A can provide support to the catheter body 271 and a drive shaft configured to drive the impeller assembly. Further, the motor assembly 206A can include a motor 220A that has a hollow lumen therethrough. Unlike the embodiments disclosed in FIGS. 4-10C, the guidewire 235 may extend through the proximal guidewire opening 237A formed proximal to the motor 220A, rather than between the motor 220A and the flow diverter 205A. A resealable member 266A may be formed in the proximal guidewire opening 237A such that the resealable member 266A can close the opening 237A when the guidewire 235 is removed from the catheter assembly. A rotary seal 273 may be disposed inside a lip of the flow diverter 205A. The rotary seal 273 may be disposed over and may contact a motor shaft extending from the motor 220A. The rotary seal 273 can act to seal fluid within the flow diverter 205A. In some embodiments, a hydrodynamic seal can be created to prevent fluid from breaching the rotary seal 273.

In the implementation of FIG. 11, the motor 220A can be permanently secured to the flow diverter 205A and catheter assembly. Because the proximal guidewire opening 237 is positioned proximal the motor, the motor 220A need not be coupled with the catheter assembly in a separate coupling step. The motor 220A and the catheter assembly can thus be disposable in this embodiment. The motor 220A can include an output shaft and rotor magnetically coupled with a rotatable magnet in the flow diverter 205A. The motor 220A can also include a plurality of windings that are energized to directly drive the rotatable magnet in the flow diverter 205A. In variations of the embodiment of FIG. 11, the motor 220A is permanently attached to the flow diverter but is off-set to provide one or more benefits to the motor assembly 206A. For example, the off-set position enables better support of the rotational components within the flow diverter or housing for the motor.

Figure 12A:
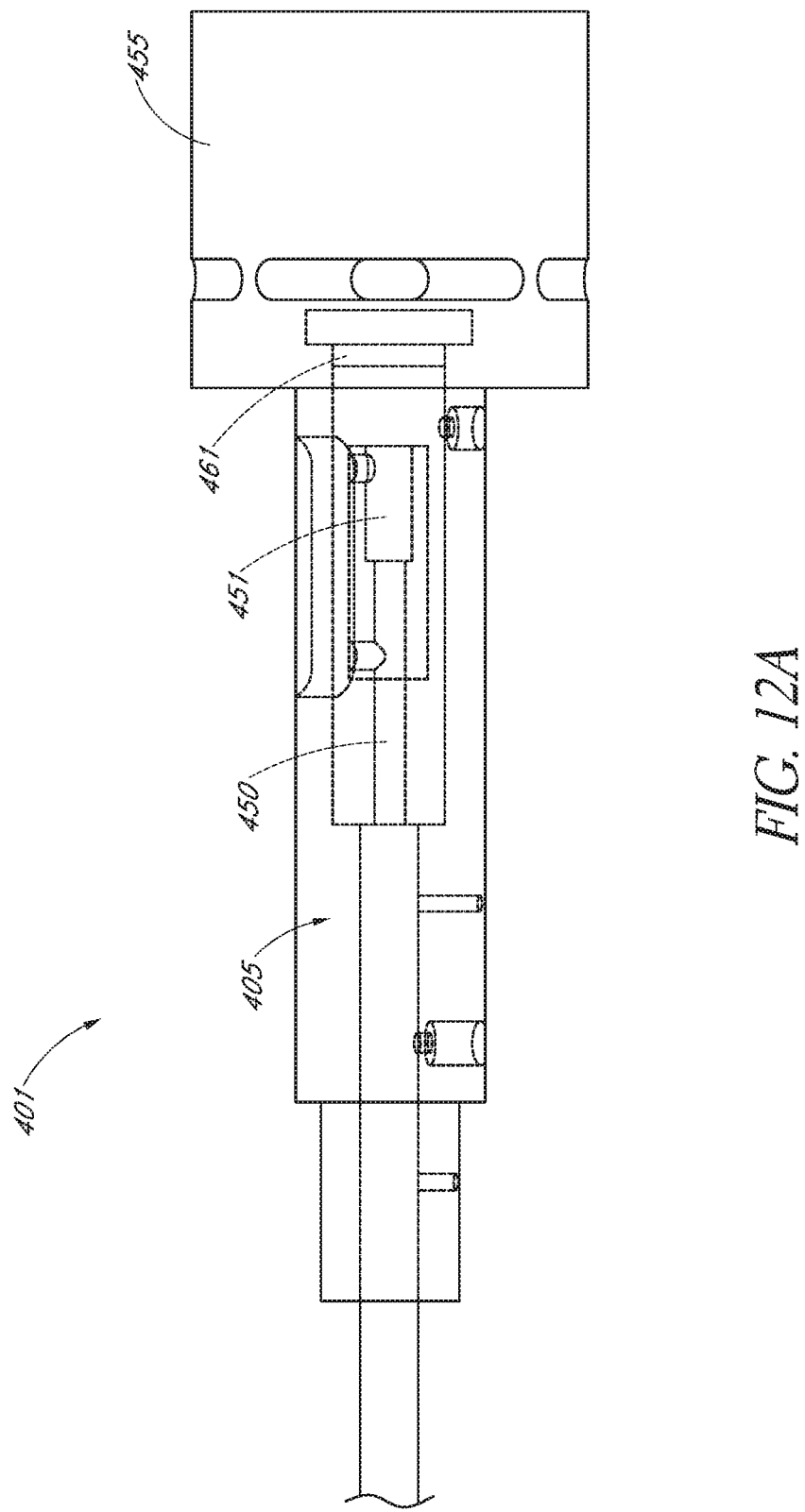
FIGS. 12A-12B illustrates side schematic views of a motor assembly according to yet another embodiment.
Figure 12B:
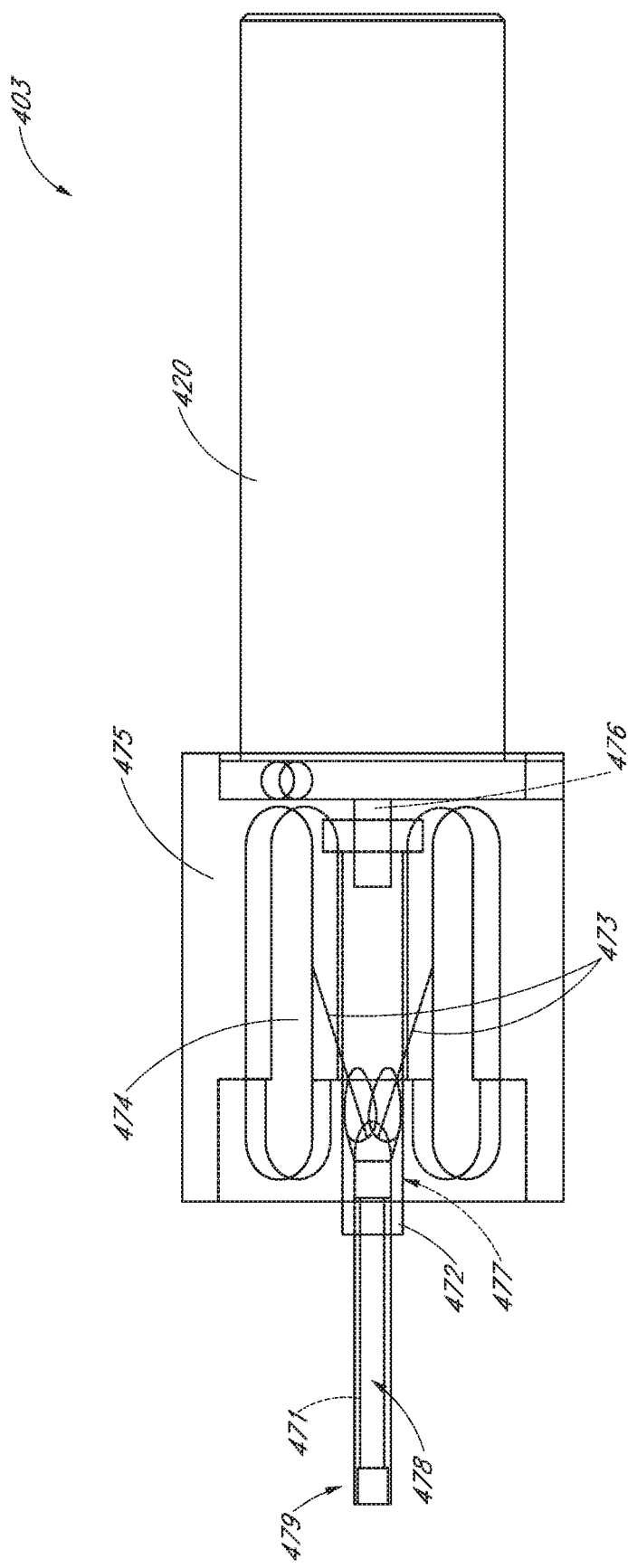

FIGS. 12A-12B illustrate another embodiment of a motor coupling having a driven assembly 401 and a drive assembly 403. Unlike the implementations disclosed in FIGS. 4-10C, however, the embodiment of FIGS. 12A-12B can include a mechanical coupling disposed between an output shaft of a motor and a proximal end of a flexible drive shaft or cable. Unlike the implementations disclosed in FIG. 11, however, the embodiment of FIGS. 12A-12B can include a guidewire guide tube that terminates at a location distal to a motor shaft 476 that extends from a motor 420. As best shown in FIG. 12B, an adapter shaft 472 can operably couple to the motor shaft 476 extending from the motor 420. A distal end portion 477 of the adapter shaft 472 can mechanically couple to a proximal portion of an extension shaft 471 having a central lumen 478 therethrough. As shown in FIG. 12B, one or more trajectories 473 can be formed in channels within a motor housing 475 at an angle to the central lumen 478 of the extension shaft 471. The motor housing 475 can enclose at least the adapter shaft 472 and can include one or more slots 474 formed through a wall of the housing 475.

In some implementations, a guidewire (not shown in FIG. 12B) may pass through the guidewire guide tube from the distal end portion of the catheter assembly and may exit the assembly through the central lumen 478 near the distal end portion 477 of the adapter shaft 472 (or, alternatively, near the proximal end portion of the extension shaft 471). In some embodiments, one of the extension shaft 471 and the adapter shaft 472 may include a resealable member disposed therein to reseal the lumen through which the guidewire passes, as explained above. In some embodiments, the extension shaft 471 and the adapter shaft 472 can be combined into a single structure. When the guidewire exits the central lumen 478, the guidewire can pass along the angled trajectories 473 which can be formed in channels and can further pass through the slots 474 to the outside environs. The trajectories 473 can follow from angled ports in the adapter shaft 472. A clinician can thereby pull the guidewire through the slots 474 such that the end of the guidewire can easily be pulled from the patient after guiding the catheter assembly to the heart chamber or other desired location. Because the guidewire may extend out the side of the housing 475 through the slots, the motor shaft 476 and motor 420 need not include a central lumen for housing the guidewire. Rather, the motor shaft 476 may be solid and the guidewire can simply pass through the slots 474 formed in the side of the housing 475.

Furthermore, the drive assembly 403 can mechanically couple to the driven assembly 401. For example, a distal end portion 479 of the extension shaft 471 may be inserted into an opening in a flow diverter housing 455. The distal end portion 479 of the extension shaft 471 may be positioned within a recess 451 and may couple to a proximal end of a drive cable 450 that is mechanically coupled to the impeller assembly. A rotary seal 461 may be positioned around the opening and can be configured to seal the motor 420 and/or motor housing 475 from fluid within the flow diverter 405. Advantageously, the embodiments of FIGS. 12A-B allow the motor 420 to be positioned proximal of the rotary seal in order to minimize or prevent exposing the motor 420 to fluid that may inadvertently leak from the flow diverter. It should be appreciated that the extension shaft 471 may be lengthened in order to further isolate or separate the motor 420 from the fluid diverter 405 in order to minimize the risk of leaking fluids. In other variations, the motor 420 is off-set from the proximal end of the driven assembly 401. For example, a tension member or other lateral drive component can be provided to engage the output shaft of the motor 420 with the driven assembly 401. A belt or other tension member (shown, e.g., in FIG. 16) can couple the output shaft with the driven assembly 401. Other lateral drive arrangements (e.g., arrangements where the motor mounted off of the rotational axis of the driven assembly 401) can employ one or more direct engagement components such as gears.

Figure 13:
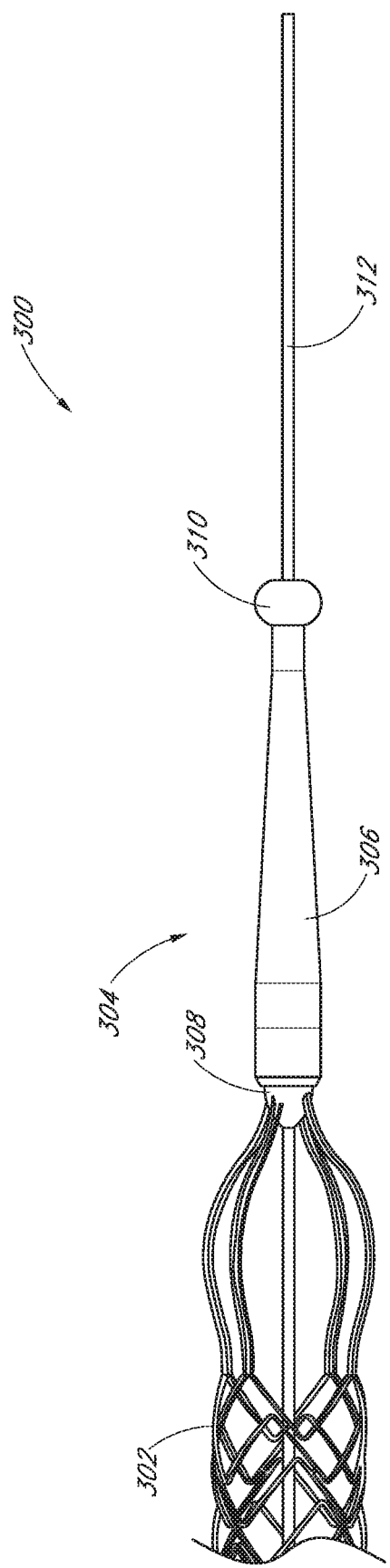
FIG. 13 is a side view of a distal tip member disposed at a distal end of the catheter assembly, according to one embodiment.

Turning to FIG. 13, further features that may be included in various embodiments are disclosed. FIG. 13 illustrates a distal end portion 300 of a catheter assembly, such as the catheter assembly 100A described above. As shown a cannula housing 302 can couple to a distal tip member 304. The distal tip member 304 can be configured to assist in guiding the operative device of the catheter assembly, e.g., an impeller assembly (which can be similar to or the same as impeller assembly 116A), along the guidewire 235. The exemplary distal tip member 304 is formed of a flexible material and has a rounded end to prevent injury to the surrounding tissue. If the distal tip member 304 contacts a portion of the patient's anatomy (such as a heart wall or an arterial wall), the distal tip member 304 will safely deform or bend without harming the patient. The tip can also serve to space the operative device away from the tissue wall. In addition, a guidewire guide tube 312, discussed above with reference to FIG. 4, can extend through a central lumen of the catheter assembly. Thus, the guidewire guide tube 312 can pass through the impeller shaft (not shown, as the impeller is located proximal to the distal end portion 300 shown in FIG. 13) and a lumen formed within the distal tip member 304. In the embodiment of FIG. 13, the guidewire guide tube 312 may extend distally past the distal end of the distal tip member 304. As explained above, in various embodiments, the clinician can introduce a proximal end of the guidewire into the distal end of the guidewire guide tube 312, which in FIG. 13 extends distally beyond the tip member 304. Once the guidewire 235 has been inserted into the patient, the guidewire guide tube 312 can be removed from the catheter assembly in some implementations.

The distal tip member 304 can comprise a flexible, central body 306, a proximal coupling member 308, and a rounded tip 310 at the distal end of the tip member 304. The central body 306 can provide structural support for the distal tip member 304. The proximal coupling member 308 can be coupled to or integrally formed with the central body 306. The proximal coupling member 308 can be configured to couple the distal end of the cannula housing 302 to the distal tip member 304. The rounded tip 310, also referred to as a ball tip, can be integrally formed with the central body 306 at a distal end of the tip member 304. Because the rounded tip 310 is flexible and has a round shape, if the tip member 304 contacts or interacts with the patient's anatomy, the rounded tip 310 can have sufficient compliance so as to deflect away from the anatomy instead of puncturing or otherwise injuring the anatomy. As compared with other potential implementations, the distal tip member 304 can advantageously include sufficient structure by way of the central body 306 such that the tip member 304 can accurately track the guidewire 235 to position the impeller assembly within the heart. Yet, because the tip member 304 is made of a flexible material and includes the rounded tip 310, any mechanical interactions with the anatomy can be clinically safe for the patient.

One potential problem with the embodiment of FIG. 13 is that it can be difficult for the clinician to insert the guidewire into the narrow lumen of the guidewire guide tube 312. Since the guidewire guide tube 312 has a small inner diameter relative to the size of the clinician's hands, the clinician may have trouble inserting the guidewire into the distal end of the guidewire guide tube 312, which extends past the distal end of the tip member 304 in FIG. 13. In addition, when the clinician inserts the guidewire into the guidewire guide tube 312, the distal edges of the guidewire guide tube 312 may scratch or partially remove a protective coating applied on the exterior surface of the guidewire. Damage to the coating on the guidewire may harm the patient as the partially uncoated guidewire is passed through the patient's vasculature. Accordingly, it can be desirable in various arrangements to make it easier for the clinician to insert the guidewire into the distal end of the catheter assembly, and/or to permit insertion of the guidewire into the catheter assembly while maintaining the protective coating on the guidewire.

Additionally, as explained herein, the cannula housing 302 (which may form part of an operative device) may be collapsed into a stored configuration in some embodiments such that the cannula housing is disposed within an outer sheath. When the cannula housing 302 is disposed within the outer sheath, a distal end or edge of the outer sheath may abut the tip member 304. In some cases, the distal edge of the outer sheath may extend over the tip member 304A, or the sheath may have an outer diameter such that the distal edge of the outer sheath is exposed. When the sheath is advanced through the patient's vasculature, the distal edge of the outer sheath may scratch, scrape, or otherwise harm the anatomy. There is a therefore a need to prevent harm to the patient's anatomy due to scraping of the distal edge of the sheath against the vasculature.

Figure 14:
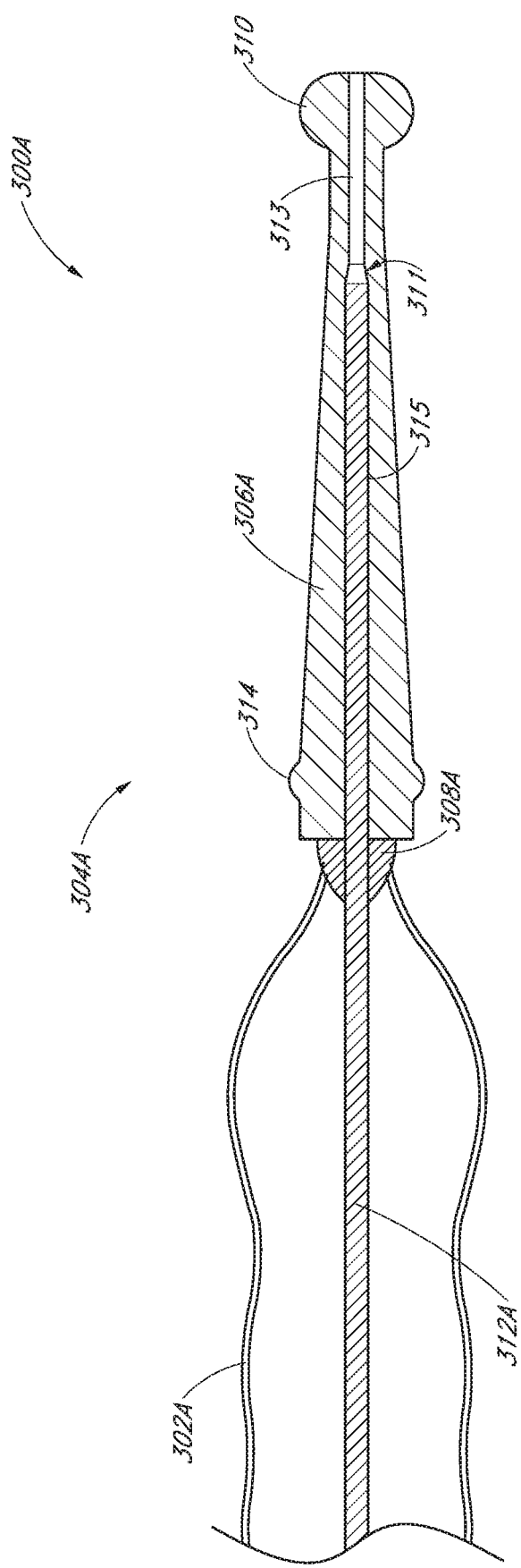
FIG. 14 is a side cross-sectional view of a distal tip member disposed at a distal end of the catheter assembly, according to another embodiment.

FIG. 14 is a side cross-sectional view of a distal tip member 304A disposed at a distal end 300A of the catheter assembly, according to another embodiment. Unless otherwise noted, the reference numerals in FIG. 14 may refer to components similar to or the same as those in FIG. 13. For example, as with FIG. 13, the distal tip member 304A can couple to a cannula housing 302A. The distal tip member 304A can include a flexible, central body 306A, a proximal coupling member 308A, and a rounded tip 310A at the distal end of the tip member 304A. Furthermore, as with FIG. 13, a guidewire guide tube 312A can pass through the cannula housing 302A and a lumen passing through the distal tip member 304A.

However, unlike the embodiment of FIG. 13, the central body 306A can include a bump 314 disposed near a proximal portion of the tip member 304A. The bump 314 illustrated in FIG. 14 may advantageously prevent the outer sheath from scraping or scratching the anatomy when the sheath is advanced through the patient's vascular system. For example, when the cannula housing 302A is disposed within the outer sheath, the sheath will advance over the cannula housing 302A such that the distal edge or end of the sheath will abut or be adjacent the bump 314 of the tip member 304A. The bump 314 can act to shield the patient's anatomy from sharp edges of the outer sheath as the distal end 300A is advanced through the patient. Further, the patient may not be harmed when the bump 314 interact with the anatomy, because the bump 314 includes a rounded, smooth profile. Accordingly, the bump 314 in FIG. 14 may advantageously improve patient outcomes by further protecting the patient's anatomy.

Furthermore, the guidewire guide tube 312A of FIG. 14 does not extend distally past the end of the tip member 306A. Rather, in FIG. 14, the central lumen passing through the tip member 304A may include a proximal lumen 315 and a distal lumen 313. As shown in FIG. 14, the proximal lumen 315 may have an inner diameter larger than an inner diameter of the distal lumen 313. A stepped portion or shoulder 311 may define the transition between the proximal lumen 315 and the distal lumen 313. As illustrated in FIG. 14, the inner diameter of the proximal lumen 315 is sized to accommodate the guidewire guide tube 312A as it passes through a portion of the tip member 304A. However, the inner diameter of the distal lumen 313 in FIG. 14 is sized to be smaller than the outer diameter of the guidewire guide tube 312A such that the guidewire guide tube 312A is too large to pass through the distal lumen 313 of the tip member 304A. In addition, in some embodiments, the thickness of the guidewire guide tube 312A may be made smaller than the height of the stepped portion or shoulder 311, e.g., smaller than the difference between the inner diameter of the proximal lumen 315 and the inner diameter of the distal lumen 313. By housing the guidewire guide tube 312A against the shoulder 311, the shoulder 311 can protect the outer coating of the guidewire when the guidewire is inserted proximally from the distal lumen 313 to the proximal lumen 315.

The embodiment illustrated in FIG. 14 may assist the clinician in inserting the guidewire (e.g., the guidewire 235 described above) into the distal end 300A of the catheter assembly. For example, in FIG. 14, the guidewire guide tube 312A may be inserted through the central lumen of the catheter assembly. For example, the guidewire guide tube 312A may pass distally through a portion of the motor, the catheter body, the impeller assembly and cannula housing 302A, and through the proximal lumen 315 of the tip member 304A. The guidewire guide tube 312A may be urged further distally until the distal end of the guidewire guide tube 312A reaches the shoulder 311. When the distal end of the guidewire guide tube 312A reaches the shoulder 311, the shoulder 311 may prevent further insertion of the guidewire guide tube 312 in the distal direction. Because the inner diameter of the distal lumen 313 is smaller than the outer diameter of the guidewire guide tube 312A, the distal end of the guidewire guide tube 312A may be disposed just proximal of the shoulder 311, as shown in FIG. 14.

The clinician may insert the proximal end of the guidewire (such as the guidewire 235 described above) proximally through the distal lumen 313 passing through the rounded tip 310A at the distal end of the tip member 304A. Because the tip member 304A is flexible, the clinician can easily bend or otherwise manipulate the distal end of the tip member 304A to accommodate the small guidewire. Unlike the guidewire guide tube 312A, which may be generally stiffer than the tip member 304A, the clinician may easily deform the tip member 304A to urge the guidewire into the distal lumen 313. Once the guidewire is inserted in the distal lumen 313, the clinician can urge the guidewire proximally past the stepped portion 311 and into the larger guidewire guide tube 312A, which may be positioned within the proximal lumen 315. Furthermore, since most commercial guidewires include a coating (e.g. a hydrophilic or antimicrobial coating, or PTFE coating), the exemplary guide tube and shoulder advantageously avoid damaging or removing the coating. When the wall thickness of the guidewire guide tube 312A is less than the height of the step or shoulder 311, the shoulder 311 may substantially prevent the guidewire guide tube 312A from scraping the exterior coating off of the guidewire. Instead, the guidewire easily passes from the distal lumen 313 to the proximal lumen 315. The guidewire may then be urged proximally through the impeller and catheter assembly until the guidewire protrudes from the proximal end of the system, such as through the proximal guidewire opening 237 described above with reference to FIG. 4.

Figure 15:
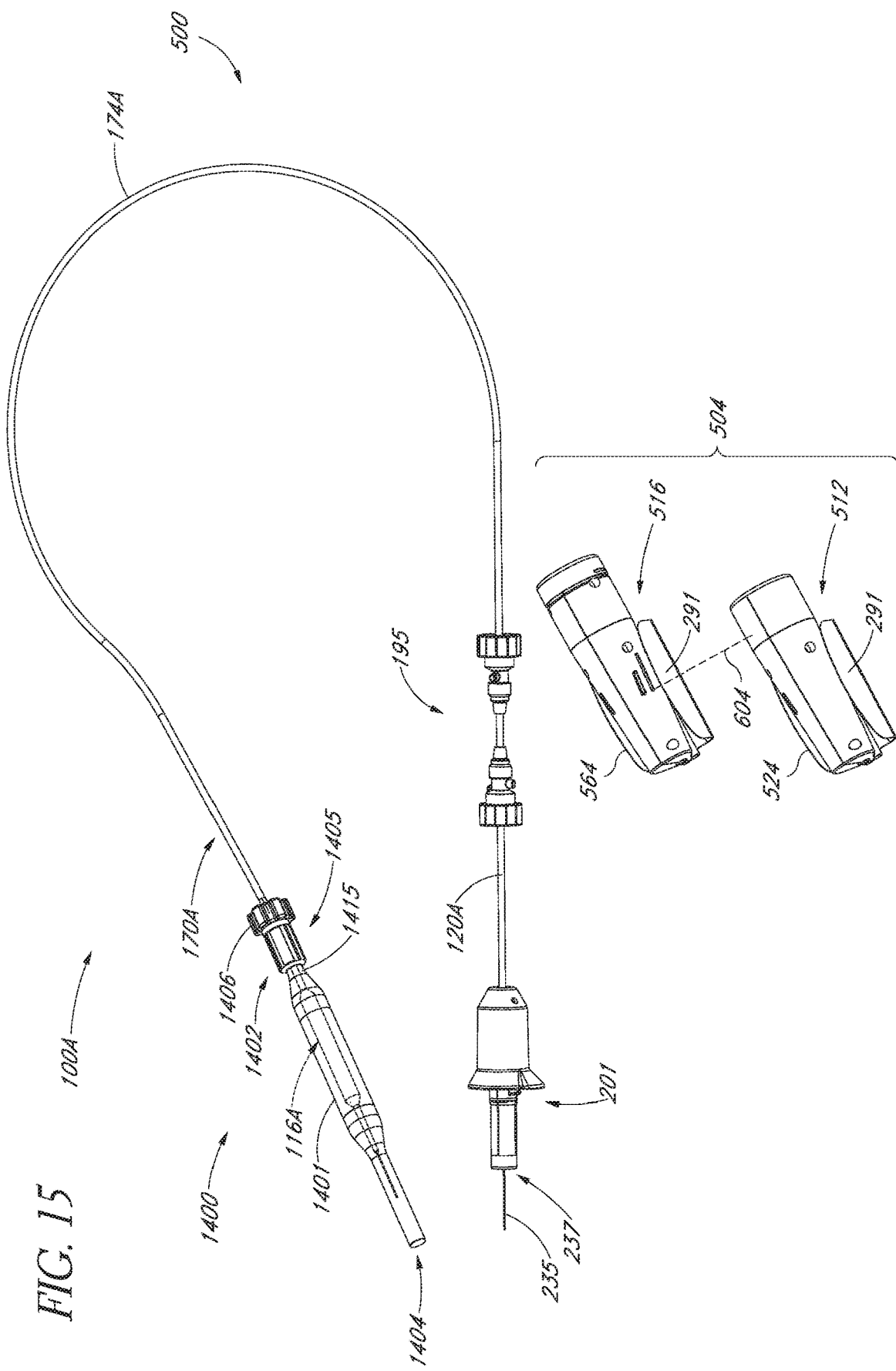
FIG. 15 illustrates a catheter pump assembly including an off-set motor drive system.
Figure 16:
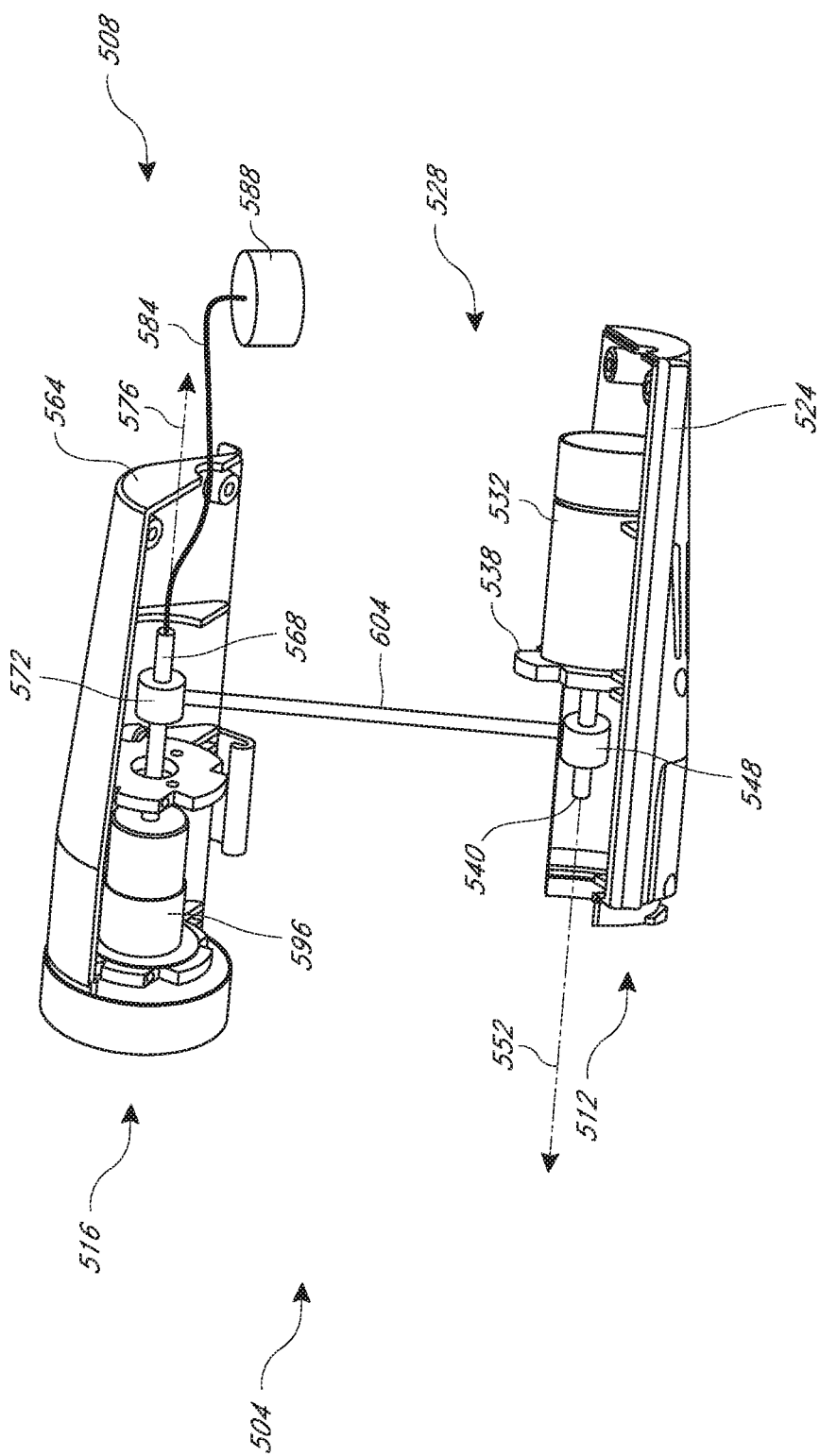
FIG. 16 is a partial assembly view of an embodiment with separate housings enclosing portions of a motor assembly and a transmission assembly.
Figure 17:
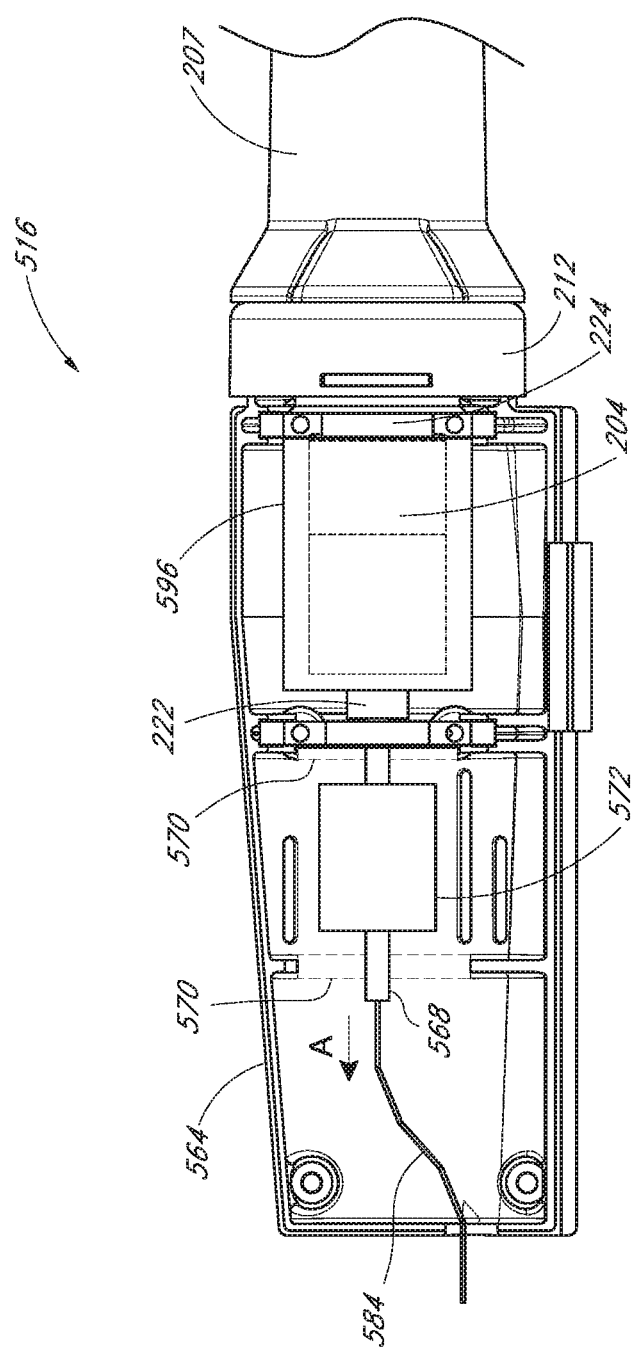
FIG. 17 is a partial assembly view showing internal components of one embodiment of a transmission assembly.

FIGS. 15-17 illustrate features of further embodiments in connection with a catheter pump assembly 500. In various respects, catheter pump assembly 500 is similar to catheter assembly 100A described above, except it includes a modified drive system 504. The assembly 500 includes the catheter assembly 100A discussed above, in some cases with some modifications as discussed below. In one variation the catheter pump assembly 500 includes a drive system 504 and a fluid removal system 508. In various respects, drive system 504 is similar to drive system 206 described above. The fluid removal system 508 can be part of an operating fluid system, for example incorporating components of the infusion system 26 discussed above and any of the additional features discussed below. The drive system 504 includes a motor assembly 512 and a transmission assembly 516 that allows the motor assembly 512 to be positioned away from or off-axis from the proximal end of the catheter assembly 100A.

In one variation the motor assembly 512 includes a housing 524 having a motor unit 528 disposed therein. The motor unit 528 includes an electric motor 532 that is electrically coupled with and controlled by a controller, e.g., by the controller 22. The housing 524 is sufficiently rigid and stable to reduce or minimize external vibrations or other environmental conditions from affecting the operation of the electric motor 532 or the components mechanically coupled therewith. This can be important to ensure the forces experienced by motor are absorbed by the housing and transmitted to stabilizing platform instead of being translated through the catheter pump assembly. One or more motor mounts 538 also can be provided to secure the motor 532 within the housing 524. The motor 532 can include an output shaft 540 that is rotated by a rotor of the motor 532. A drive component 548 is coupled with, e.g., mounted on, the output shaft 540 such that the shaft 540 and the drive component 548 are rotated about a first axis 552.

The transmission assembly 516 can be located at least in part in a housing 564 that is separate from the housing 524. In one embodiment, the housing 564 has a shaft 568 disposed therein and journaled for rotation. The shaft 568 can be supported by bearings 570 disposed on proximal and distal ends thereof. In one embodiment, a driven component 572 can be coupled with, e.g., mounted on, the shaft 568. The shaft 568 and the driven component 572 can freely rotate in the housing 564 about a second axis 576, which can be offset from the first axis 552.

The shaft 568 preferably includes a lumen that can be fluidly coupled at a distal end thereof with a proximal portion of the infusion or operating fluid system 26 and at a proximal end thereof with a conduit 584 to convey the fluid to a waste vessel 588. The lumen in the shaft, the conduit 584 and the vessel 588 can all be part of the fluid removal system 508. In certain embodiment, the operating fluid from the system 26 is directed into the catheter assembly 100A and at least a portion flows proximally over certain components of the catheter assembly 100A. For example, a rotatable magnet can be mounted to rotate in the flow diverter housing 207. This rotating structure is sometimes referred to herein as a rotor. In order to provide smooth and durable operation it is desirable to subject the rotor to a fluid to cool and/or lubricate the rotor. This fluid flows most efficiently within the catheter assembly 100A if it can flow in a distal to proximal path within the catheter assembly 100A. For example, one advantageous path is illustrated by arrow A from a distal end of the rotor to a proximal end of the rotor, and thereafter into the lumen in the shaft 568 and out of the transmission assembly 516. US Patent Application Publication No. 2012/0178986 is incorporated by reference herein in its entirety for all purposes, and in some respects for additional discussion of flow paths in connection with rotors.

The driven component 572 can be located in a proximal portion of the housings 564. The driven component 572 and the drive component 548 comprise working portions of a power train between the motor and the catheter assembly 100A. These component can take a conventional form, e.g., as gears, sprockets, pulleys, or variable torque members.

A distal portion of the housing 564 can enclose a drive component 596 configured to be rotated with the shaft 568. The drive component 596 is sometimes described as a second drive component and the drive component 548 is sometimes referred to as a first drive component herein. The use of "first" and "second" in this context is arbitrary with the "first" member being closer to the source of torque, e.g., the motor 532. The drive component 596 is configured to be engaged with the proximal end of the catheter assembly 100A in the same way discussed above, e.g., with paired permanent magnets, or with gears or other direct contact mechanical interface. For example, the drive component 596 can comprise a cup-like structure that can receive the proximal end of the catheter assembly 100A. When so received, a driven component of the catheter assembly 100A such as a rotor or other member including magnets, such as the magnets 204, is engaged with the drive component 596.

FIGS. 15 and 16 show that the catheter pump assembly 500 includes a tension member 604 that extends between the motor assembly 512 and the driven component 572 of the transmission assembly 516. The tension member 604 can be considered part of the transmission assembly 516. The driven component 572, which can include or be coupled with the magnets 204, can be coupled with an elongate flexible member such as the drive shaft 208. The tension member 604 can be coupled with the motor unit 528 and with the driven component 572, including the magnet or magnets 204, to cause the driven component 572 to rotate when the motor 532 rotates and thereby cause the drive shaft 208 (or other elongate flexible member) and the impeller assembly 92 to rotate.

The tension member 604 can take any suitable form that is suitable for transferring torque between the drive and driven members 548, 572 as will be understood by one of skill from the description herein. For example, the tension member 604 can comprise a drive belt such as a tooth belt, a cog belt, a notch belt, a V-belt. The tension member 604 can comprise a chain or other flexible driving member. In an embodiment where the tension member 604 is a chain, a tooth belt, a cog belt, a notch belt, or similar structure, the drive and driven members 548, 572 can be cogs.

FIGS. 15-17 illustrate the pump catheter pump assembly 500 comprising two separate housings. In other embodiment the transmission assembly 516 and the motor assembly 512 are disposed in the same housing. Separate or separable housings are advantageous in facilitating one or more reusable components. For example, in one embodiment, the transmission assembly 516 is reusable. In another embodiment, the motor assembly 512 is reusable. In some embodiments, the transmission assembly 516 can be used a first number of times. In some embodiments, the motor assembly 512 can be used a second number of times greater than the first number of times.

The motor assemblies discussed herein and systems incorporating them provide many advantages. For example, sterilizing the components of the catheter pumps incorporating one or more features discussed herein can be facilitated by separating the driven assembly 201 from the motor unit 528 or the motor assembly 14A, That is, in various methods of use, a catheter assembly can be sterilized apart from a motor assembly or motor unit and/or transmission assembly. In various methods of use, the motor assembly or motor unit and/or transmission assembly can be sterilized and reused whereas the catheter assembly can be disposable. By providing transfer of rotation through a tension member, the drive components coupled with the motor unit or motor assembly and coupled with the proximal end of the catheter assembly can easily be decoupled or disassembled for separate sterilization.

Further, as discussed above the using a tension member to transfer torque from the motor unit or motor assembly provides for isolation or insulation between the catheter assembly and the motor. Mechanical isolation of the motor from the catheter assembly is useful in that due to normal manufacturing variation in the components of the motor, there may be noticeable vibration upon operation of the motor. The tension member can absorb some of that vibration and reduce the amplitude or frequency of the vibration as felt by the catheter assembly. Also, the drive component coupled with the proximal end of the catheter assembly can be better supported so that such drive component has less or no eccentricity in rotation.

The separation of the motor unit or motor assembly from the catheter assembly also enables isolation of the heat of the motor from the proximal end of the catheter assembly. Certain advantageous motor designs generate significant heat. For example, the motor assembly 14A induces rotation by driving current through coils to generate magnetic fields. It is preferred that the proximal end of the catheter assembly be adjacent to the patient, and in some cases mounted on the patient's leg or otherwise directly contacting the patient. The off-set positioning of the motor assembly 14A enables the heat generating components to be isolated or insulated from the patient while still permitting the proximal end of the catheter assembly to be at or on the patient. Regardless of the type of motor used, higher speeds generally generate more heat. Therefore, for higher rotational speeds it is more important to provide for heat isolation or insulation between the heat generating components (e.g., the motor or mechanical bearings) and the patient. In at least this sense, these arrangements insulate the components from each other. By reducing or minimizing heat transfer from the motor unit or motor assembly to the catheter assembly heating of fluids in the catheter assembly is reduced or minimized which can facilitate longer operation, higher biocompatibility, and/or more convenient operation by the medical staff overseeing the use of the catheter pumps described herein.

The off-set positioning of the motor unit or motor assembly also allows the movements of the catheter assembly to not be felt by or to be only minimally felt by the motor unit or motor assembly. Any such movement or heat generated by the catheter assembly can be isolated from and thus prevented from compromising or damaging the motor.

The structures above provide for modular use of components. For example robust locking devices can be provided between housings (see, e.g., the structures of FIG. 9 and corresponding description) enabling the catheter assembly can be securely connected to a transmission assembly. As such any of the transmission assembly, a tension member (such as a belt), and a motor assembly or motor unit can be reused one or more times while the catheter assembly will generally be disposed of in each use.

By providing the motor unit or motor assembly offset from the proximal end of the catheter assembly, enhanced sealing and operating fluid removal can be provided. FIG. 16 shows that operating fluid can be removed from the proximal end of the catheter assembly rather than being diverted through a more complex manifold out of a side portion of the catheter assembly. This relieves the need to pressure-seal the catheter assembly at a location distal of the drive component disposed within the catheter assembly. This arrangement is also more tolerant of small breaches in seals. That is, the operating fluid may be a biocompatible fluid such as saline. Such a fluid can be corrosive to the motor unit or motor assembly. By off-setting the motor unit or motor assembly from flow path of the operating fluid small leaks in fluid will not be directed to the motor but rather will be located at or in the transmission assembly. While this may limit the re-use of the transmission assembly, the motor unit or motor assembly may be unaffected by minor seal breaches and thus can remain capable of re-use.

In certain embodiments, a guidewire passage is provided through an assembly including the catheter assembly and the transmission assembly. This passage enables easier access to a guidewire and in some cases reintroduction of a guidewire into a system when partially engaged. In particular, the transmission assembly may be coupled with the catheter assembly while retaining the ability to advance the catheter assembly over the guidewire. This can be achieved by directing the guidewire through the same channel that the operating fluid flows, e.g., to exit the proximal end of the catheter assembly and/or transmission assembly. This allows the clinician some flexibility in the order of assembly and/or more convenient repositioning without fully disassembling the motor unit/assembly, transmission assembly, and catheter assembly.

These arrangements can help to reduce the cost of having and operating the catheter pump 10. For example, one or more components can be treated as capital equipment with the cost of such components being defrayed over many uses. In specific implementations, the console, the motor unit or motor assembly, and the transmission assembly can be re-used many times and the catheter assembly and the tension member (e.g., belt) can be disposed of after one or more uses.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A catheter pump assembly, comprising:
    an elongate body having a proximal end, a distal end and at least one lumen extending therebetween;
    an elongate flexible shaft having a proximal end and a distal end and extending through the lumen;
    an impeller coupled with the distal end of the elongate flexible shaft;
    a motor having a first drive component coupled therewith, the first drive component rotatable about a first axis; and
    a second drive component coupled with the proximal end of the elongate flexible shaft, the second drive component rotatable about a second axis that is offset from the first axis;
    wherein the motor drives the first and second drive component, the second drive component and the first drive component proximal of the elongate flexible shaft.

2. The catheter pump of claim 1, further comprising a tension member coupled with the first and second drive component to cause the second drive component to rotate when the motor rotates, and thereby to cause the elongate flexible shaft and the impeller to rotate.

3. The catheter pump assembly of claim 2, wherein the tension member comprises a flexible belt.

4. The catheter assembly of claim 2, further comprising:
    a first transmission housing disposed at the proximal end of the elongate body;
    a third drive component rotatable within the first transmission housing, the third drive component coupled with the proximal end of the elongate flexible shaft; and
    a second transmission housing having an enclosed space therein and an open end configured to receive the first transmission housing, the second transmission housing enclosing the second drive component and at least a portion of the tension member.

5. The catheter pump assembly of claim 4, wherein the third drive component and the second drive component comprise at least one magnet to provide magnetic coupling therebetween.

6. A catheter pump assembly of claim 1, wherein the second drive component comprises a driven sprocket and the first drive component comprises a drive sprocket coupled with an output shaft of the motor.

7. The catheter pump assembly of claim 2, further comprising a housing disposed around the motor and at least a portion of the tension member.

8. The catheter pump assembly of claim 7, wherein the housing enclosing the motor is separate from the second housing.

9. The catheter pump assembly of claim 1, further comprising a shaft journaled in a housing, the second drive component comprising a first speed and torque transfer member mounted on the shaft and coupled with the first drive component, and a second speed and torque output member disposed adjacent to an open end of the housing.

10. The catheter pump assembly of claim 9, wherein the shaft comprises a hollow lumen disposed therein in fluid communication with at least one lumen of the elongate body of the catheter assembly and with a waste vessel.

* * * * *